United States Patent
Oshlack et al.

(10) Patent No.: US 6,335,033 B2
(45) Date of Patent: *Jan. 1, 2002

(54) MELT-EXTRUSION MULTIPARTICULATES

(75) Inventors: Benjamin Oshlack, New York, NY (US); Hua-Pin Huang, Englewood Cliffs; Mark Chasin, Manalapan, both of NJ (US)

(73) Assignee: Euro-Celtique, S.A., Luxembourg (LU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/358,828

(22) Filed: Jul. 22, 1999

Related U.S. Application Data

(63) Continuation of application No. 08/334,209, filed on Nov. 4, 1994, now Pat. No. 5,965,161.

(51) Int. Cl.[7] .............................. A61K 9/16; A61K 9/52
(52) U.S. Cl. ....................... 424/457; 424/451; 424/452; 424/456; 424/489; 424/488; 424/487; 514/772.6; 514/781; 514/784; 514/785; 514/786; 514/951; 514/962
(58) Field of Search ................................. 424/457, 458, 424/489, 456, 468, 451, 452, 486, 487, 488

(56) References Cited

U.S. PATENT DOCUMENTS

| | | | |
|---|---|---|---|
| 2,738,303 A | 3/1956 | Blythe et al. | ................. 167/82 |
| 3,065,143 A | 11/1962 | Christenson et al. | ....... 424/468 |

(List continued on next page.)

FOREIGN PATENT DOCUMENTS

| | | | |
|---|---|---|---|
| AU | 57224 | 5/1986 | .......... A61K/47/00 |
| AU | 8976091 | 6/1992 | ........... A23L/01/09 |

(List continued on next page.)

OTHER PUBLICATIONS

Nicolas Follonier1, Eric Doelker and Ewart T. Cole, Evaluation of Hot–Melt Extrusion as a New Technique for the Production of Polymer–Based Pellets for Sustained Release Capsules containing high loadings of freely soluble drugs, Drug Development and Industrial Pharmacy, 20(8), 1323–1339 (1994).

Nicolas Follonier[1], Erick Doelker[1] and Ewart T. Cole[2], Hot–Melt Extruded Pellets for the Sustained Release of Highly Dosed Freely Solluble Drugs, Proceed. Intern. Symp. COntrol. Rel. Bioact. Mater., 18(1991), pp. 578–579.

Twin Screw Extrusion in the Production of Novel Dosage Forms, Pharmaceutical Manufacturing Review (Jun. 1994).

Follonier, Nicolas, et al., "Hot–Melt Extruded Pellets For The Sustained Release Of Higly Dosed Freely Soluble Drugs", *Capsule News*, vol. 1, No. 3, Edited by Roland Daumesnil, (Jun./Jul. 1991).

(List continued on next page.)

*Primary Examiner*—James M. Spear
(74) *Attorney, Agent, or Firm*—Davidson, Davidson & Kappel, LLC

(57) ABSTRACT

A unit dose sustained-release oral dosage form containing a plurality of melt-extruded particles, each consisting essentially of a therapeutically active agent, one or more retardants, and an optional water-insoluble binder is disclosed. The particles have a length of from about 0.1 to about 12 mm and can be of varying diameters and each unit dose provides a release of therapeutically active agents over at least about 8 hours. Methods of preparing the unit doses as well as extrusion processes and methods of treatment are also disclosed.

43 Claims, 10 Drawing Sheets

U.S. PATENT DOCUMENTS

| | | | |
|---|---|---|---|
| 3,652,589 A | 3/1972 | Flick et al. ............ 260/326.5 M |
| 3,714,350 A | 1/1973 | Gough ..................... 424/203 |
| 3,830,934 A | 8/1974 | Flick et al. ................ 424/330 |
| 3,845,770 A | 11/1974 | Theeuwes et al. ........... 128/260 |
| 3,880,991 A | 4/1975 | Yolles ..................... 424/22 |
| 3,950,508 A | 4/1976 | Mony et al. ................. 424/19 |
| 3,965,256 A | 6/1976 | Leslie ...................... 424/22 |
| 3,974,157 A | 8/1976 | Shetty et al. ........ 260/247.2 B |
| 4,013,784 A | 3/1977 | Speiser .................... 424/19 |
| 4,076,798 A | 2/1978 | Casey et al. ............... 424/419 |
| 4,132,753 A | 1/1979 | Blichare et al. ............. 264/25 |
| 4,173,417 A | 11/1979 | Kruder ..................... 366/89 |
| 4,230,687 A | 10/1980 | Sair et al. .................. 424/22 |
| 4,259,314 A | 3/1981 | Lowey ...................... 424/19 |
| 4,265,875 A | 5/1981 | Byrne et al. ................ 424/19 |
| 4,292,300 A | 9/1981 | Byrne et al. ................ 424/19 |
| 4,310,483 A | 1/1982 | Dorfel et al. .............. 264/117 |
| 4,343,789 A | 8/1982 | Kawata et al. ............. 424/461 |
| 4,344,431 A | 8/1982 | Yolles .................... 128/260 |
| 4,346,709 A | 8/1982 | Schmitt ................... 128/260 |
| 4,366,172 A | 12/1982 | Lednicer .................. 424/330 |
| 4,374,082 A | 2/1983 | Hochschild ............... 264/129 |
| 4,380,534 A | 4/1983 | Fukui et al. ............... 264/38 |
| 4,389,393 A | 6/1983 | Schor et al. ................ 424/19 |
| 4,406,883 A | 9/1983 | Byrne et al. ............... 424/80 |
| 4,421,736 A | 12/1983 | Walters et al. .............. 424/21 |
| 4,483,847 A | 11/1984 | Augart ..................... 424/22 |
| 4,533,562 A | 8/1985 | Ikegami et al. ............... 427/3 |
| 4,613,619 A | 9/1986 | Sleigh et al. .............. 514/546 |
| 4,621,114 A | 11/1986 | Watanabe ................. 524/451 |
| 4,649,042 A | 3/1987 | Davis et al. ............... 424/438 |
| 4,720,384 A | 1/1988 | DiLuccio et al. ............ 424/78 |
| 4,764,378 A | 8/1988 | Keith et al. ............... 424/435 |
| 4,778,676 A | 10/1988 | Yang et al. ................. 424/79 |
| 4,801,458 A | 1/1989 | Hidaka et al. ............. 424/443 |
| 4,801,460 A | 1/1989 | Goertz et al. ............. 424/465 |
| 4,806,337 A | 2/1989 | Snipes et al. ................ 71/65 |
| 4,818,450 A | 4/1989 | Hall et al. .................. 264/39 |
| 4,828,836 A | 5/1989 | Elger et al. ............... 424/419 |
| 4,834,984 A | 5/1989 | Goldie et al. .............. 424/488 |
| 4,842,761 A | 6/1989 | Rutherford ................. 252/90 |
| 4,844,907 A | 7/1989 | Elger et al. ............... 424/465 |
| 4,844,909 A | 7/1989 | Goldie et al. .............. 424/480 |
| 4,861,598 A | 8/1989 | Oshlack ................... 424/468 |
| RE33,093 E | 10/1989 | Schiraldi et al. ............ 424/676 |
| 4,879,108 A | 11/1989 | Yang et al. ................ 424/440 |
| 4,880,585 A | 11/1989 | Klimesch et al. ........... 264/141 |
| 4,880,830 A | 11/1989 | Rhodes .................... 424/470 |
| 4,882,151 A | 11/1989 | Yang et al. ................ 424/440 |
| 4,882,152 A | 11/1989 | Yang et al. ................ 424/440 |
| 4,882,153 A | 11/1989 | Yang et al. ................ 424/440 |
| 4,882,155 A | 11/1989 | Yang et al. ................ 424/440 |
| 4,882,156 A | 11/1989 | Yang et al. ................ 424/440 |
| 4,882,157 A | 11/1989 | Yang et al. ................ 424/440 |
| 4,882,159 A | 11/1989 | Yang et al. ................ 424/440 |
| 4,882,167 A | 11/1989 | Jang ....................... 424/468 |
| 4,894,234 A | 1/1990 | Sharma et al. ............. 424/440 |
| 4,917,899 A | 4/1990 | Geoghegan et al. ........... 424/19 |
| 4,925,675 A | 5/1990 | Giannini et al. ............. 424/78 |
| 4,935,246 A | 6/1990 | Ahrens .................... 424/490 |
| 4,957,681 A | 9/1990 | Klimesch et al. ........ 264/211.23 |
| 4,959,208 A | 9/1990 | Chakrabarti et al. .......... 424/78 |
| 4,967,486 A | 11/1990 | Doelling .................... 34/1 |
| 4,970,075 A | 11/1990 | Oshlack ................... 424/451 |
| 4,987,136 A | 1/1991 | Kreek et al. ............... 514/282 |
| 4,990,341 A | 2/1991 | Goldie et al. .............. 424/484 |
| 4,992,100 A | 2/1991 | Koepff et al. ............. 106/125 S |
| 4,994,227 A | 2/1991 | Dietz et al. ............. 264/328.16 |
| 5,007,790 A | 4/1991 | Shell ..................... 424/451 |
| 5,013,306 A | 5/1991 | Solomon et al. ............ 604/265 |
| 5,023,089 A | 6/1991 | Sakamoto et al. ........... 424/502 |
| 5,026,560 A | 6/1991 | Makino et al. ............. 424/494 |
| 5,030,400 A | 7/1991 | Danielson et al. ........... 264/101 |
| 5,035,509 A | 7/1991 | Kruder ..................... 366/89 |
| 5,049,394 A | 9/1991 | Howard et al. ............. 424/490 |
| 5,055,307 A | 10/1991 | Tsuru et al. ............... 424/693 |
| 5,073,379 A | 12/1991 | Klimesch et al. ........... 424/467 |
| 5,102,668 A | 4/1992 | Eichel et al. .............. 424/490 |
| 5,126,145 A | 6/1992 | Evenstad .................. 424/465 |
| 5,132,142 A | 7/1992 | Jones et al. ............... 427/196 |
| 5,133,974 A | 7/1992 | Paradissis et al. .......... 424/480 |
| 5,162,117 A | 11/1992 | Stupak et al. .............. 424/475 |
| 5,165,952 A | 11/1992 | Solomon et al. .............. 427/2 |
| 5,167,964 A | 12/1992 | Muhammed et al. ........ 424/482 |
| 5,169,645 A | 12/1992 | Shukla et al. .............. 424/499 |
| 5,178,868 A | 1/1993 | Malmqvist -Granlund et al. .......... 424/490 |
| 5,183,690 A | 2/1993 | Carr et al. ............. 427/213.31 |
| 5,196,203 A | 3/1993 | Boehm ..................... 424/490 |
| 5,202,128 A | 4/1993 | Morella et al. ............ 424/469 |
| 5,204,119 A | 4/1993 | Shiobara et al. ............ 424/489 |
| 5,229,148 A | 7/1993 | Copper ..................... 426/5 |
| 5,234,697 A | 8/1993 | Sipos ..................... 424/490 |
| 5,240,400 A | 8/1993 | Fujimoto et al. ........... 425/310 |
| 5,262,172 A | 11/1993 | Sipos ..................... 424/490 |
| 5,266,331 A | 11/1993 | Oshlack et al. ............ 424/468 |
| 5,271,934 A | 12/1993 | Goldberg et al. ........... 424/401 |
| 5,273,758 A | 12/1993 | Royce ..................... 424/465 |
| 5,283,065 A | 2/1994 | Doyon et al. .............. 424/467 |
| 5,290,560 A | 3/1994 | Autant et al. .............. 424/438 |
| 5,292,461 A | 3/1994 | Juch et al. ................. 264/37 |
| 5,296,266 A | 3/1994 | Kunugi et al. ............. 427/213 |
| 5,300,300 A | 4/1994 | Egidio et al. .............. 424/456 |
| 5,330,766 A * | 7/1994 | Morella et al. ............ 424/490 |
| 5,340,581 A | 8/1994 | Tseng et al. ............... 424/401 |
| 5,350,584 A | 9/1994 | McClelland et al. ........ 424/501 |
| 5,354,856 A | 10/1994 | Kawashima et al. ........ 536/127 |
| 5,356,635 A | 10/1994 | Raman et al. .............. 424/484 |
| 5,378,462 A * | 1/1995 | Boedecker et al. ....... 424/94.29 |
| 5,380,535 A | 1/1995 | Geyer et al. ............... 424/484 |
| 5,395,626 A | 3/1995 | Kotwal et al. ............. 424/472 |
| 5,403,593 A | 4/1995 | Royce ..................... 424/489 |
| 5,443,846 A | 8/1995 | Yoshioka et al. ........... 424/498 |
| 5,451,424 A | 9/1995 | Solomon et al. ............. 427/2.1 |
| 5,453,283 A | 9/1995 | Munch et al. .............. 424/489 |
| 5,456,923 A | 10/1995 | Nakamichi et al. ......... 424/489 |
| 5,472,710 A | 12/1995 | Klokkers-Bethke et al. 424/468 |
| 5,476,528 A | 12/1995 | Trimm et al. ................ 71/21 |
| 5,478,577 A | 12/1995 | Sackler et al. ............. 424/468 |
| 5,510,114 A | 4/1996 | Borella et al. ............. 424/452 |
| 5,516,205 A | 5/1996 | Oda et al. ................... 366/75 |
| 5,552,159 A | 9/1996 | Mueller et al. ............. 424/464 |
| 5,567,439 A | 10/1996 | Myers et al. .............. 424/486 |

FOREIGN PATENT DOCUMENTS

| | | | |
|---|---|---|---|
| CA | 2082573 | 5/1993 | .......... A61K/47/38 |
| CA | 2131350 | 3/1995 | ......... A61K/31/135 |
| CA | 2150304 | 12/1995 | ............. B01J/2/20 |
| DE | 2439538 | 3/1976 | ............ A61K/9/22 |
| DE | 3602360 | 7/1987 | ........... B65G/65/06 |
| DE | 3602370 | 8/1987 | .......... A61K/45/06 |
| DE | 3623193 | 1/1988 | ......... A61K/31/205 |
| DE | 4329794 | 3/1995 | ......... A61K/31/135 |
| EP | 0032004 | 12/1980 | ............ A61K/9/22 |
| EP | 0097523 | 8/1983 | ............ A61K/9/26 |
| EP | 0043254 | 5/1984 | ............ A61K/9/26 |
| EP | 0108218 | 5/1984 | ............ A61K/9/22 |
| EP | 0147780 | 12/1984 | ............ A61K/9/32 |
| EP | 0152379 | 8/1985 | ............ A61K/9/50 |
| EP | 0214735 | 7/1986 | ............ A61K/9/22 |
| EP | 0189861 | 8/1986 | .......... A61K/47/00 |

| | | | | | | | |
|---|---|---|---|---|---|---|---|
| EP | 0204596 | 12/1986 | ............ A61K/9/16 | GB | 1405088 | 6/1971 | ............ A61K/9/26 |
| EP | 204596 | 12/1986 | ............ A61K/9/14 | GB | 1504553 | 3/1978 | .......... A61K/47/00 |
| EP | 0208144 | 1/1987 | ............ A61K/9/16 | GB | 1513166 | 6/1978 | ............. B29B/1/02 |
| EP | 0248548 | 5/1987 | ............ A61K/9/22 | GB | 2030861 | 4/1980 | ............. A61J/3/08 |
| EP | 0249347 | 5/1987 | ......... A61K/31/485 | GB | 2111386 | 12/1982 | ............ A61K/9/20 |
| EP | 0251459 | 5/1987 | ............ A61K/9/22 | GB | 2117239 | 3/1983 | ............ A61K/9/20 |
| EP | 0253104 | 6/1987 | ............ A61K/9/00 | GB | 2053681 | 4/1984 | ............ A61K/9/22 |
| EP | 0240904 | 10/1987 | ............ A61K/9/20 | GB | 2196848 | 5/1988 | ............ A61K/9/22 |
| EP | 0240906 | 10/1987 | ............. A61J/3/10 | GB | 2207355 | 1/1991 | .......... A61M/31/00 |
| EP | 0254978 | 2/1988 | ............ A61K/9/22 | GB | 2246514 | 2/1992 | ............ A61K/9/16 |
| EP | 0256127 | 2/1988 | ............ C12N/9/00 | GB | 2281204 | 3/1995 | ............ A61K/9/16 |
| EP | 0267702 | 5/1988 | ............ A61K/9/14 | GB | 2284760 | 6/1995 | ............ A61K/9/16 |
| EP | 0271193 | 6/1988 | ......... A61K/31/485 | JP | 5257315 | 5/1977 | ............ A61K/9/22 |
| EP | 0275834 | 7/1988 | ............ A61K/9/20 | JP | 2223513 | 9/1990 | ............ A61K/9/10 |
| EP | 0300897 | 7/1988 | ............ A61K/9/22 | JP | 2223533 | 9/1990 | .......... A61K/47/14 |
| EP | 0021129 | 9/1988 | ............ A61K/9/16 | JP | WO 9218106 | 10/1992 | ............ A61K/9/14 |
| EP | 0295212 | 12/1988 | .......... A61K/47/00 | WO | 9104015 | 4/1991 | ............ A61K/9/16 |
| EP | 0327295 | 8/1989 | ............ A61K/9/52 | WO | 9119484 | 12/1991 | ............ A61K/9/16 |
| EP | 0337256 | 10/1989 | ............ A61K/9/20 | WO | 9119485 | 12/1991 | ............ A61K/9/16 |
| EP | 0068450 | 1/1990 | ............ A61K/9/20 | WO | 9201446 | 2/1992 | ............ A61K/9/50 |
| EP | 0351580 | 1/1990 | ............ A61K/9/22 | WO | 9202209 | 2/1992 | ............ A61K/9/22 |
| EP | 0377518 | 1/1990 | ............ A61K/9/52 | WO | 9205774 | 4/1992 | ............ A61K/9/18 |
| EP | 0354345 | 2/1990 | ............ C09H/9/04 | WO | 9206679 | 4/1992 | ............ A61K/9/16 |
| EP | 0358105 | 3/1990 | ............. A61J/3/10 | WO | 9222283 | 12/1992 | ............ A61K/9/02 |
| EP | 0358107 | 3/1990 | ............ A61K/9/20 | WO | 9300063 | 1/1993 | ............. A61J/3/00 |
| EP | 0361680 | 4/1990 | ............ A61K/9/46 | WO | 9300076 | 1/1993 | ............ A61K/9/51 |
| EP | 0361910 | 4/1990 | ............ A61K/9/16 | WO | 9304675 | 3/1993 | .......... A61K/31/16 |
| EP | 0368247 | 5/1990 | ............ A61K/9/26 | WO | WO 9307859 | 4/1993 | ............ A61K/9/16 |
| EP | 0375063 | 6/1990 | ............ A61K/9/18 | WO | 9307861 | 4/1993 | ............ A61K/9/50 |
| EP | 0377517 | 7/1990 | ......... A61K/31/52 | WO | 9310765 | 6/1993 | ............ A61K/9/22 |
| EP | 0298355 | 11/1990 | ............ A61K/9/50 | WO | 9317667 | 9/1993 | ............ A61K/9/16 |
| EP | 0415693 | 3/1991 | ......... A61K/37/02 | WO | WO 9318753 | 9/1993 | ............ A61K/9/16 |
| EP | 0430287 | 6/1991 | ............ A61K/9/54 | WO | 9324110 | 12/1993 | ............ A61K/9/20 |
| EP | 0463833 | 6/1991 | ............ A61K/9/26 | WO | WO 9324110 | 12/1993 | ............ A61K/9/20 |
| EP | 0241615 | 9/1991 | ............ A61K/9/22 | WO | 9403160 | 2/1994 | ............ A61K/9/32 |
| EP | 0452145 | 10/1991 | ............ A61K/9/14 | WO | 9403161 | 2/1994 | ............ A61K/9/52 |
| EP | 0239983 | 11/1991 | ............. A61J/3/06 | WO | 9405262 | 3/1994 | ............ A61K/9/16 |
| EP | 0465338 | 1/1992 | ............ A61K/9/16 | WO | WO 9408568 | 4/1994 | ............ A61K/9/26 |
| EP | 0481600 | 4/1992 | ............ A61L/15/28 | WO | 9422431 | 10/1994 | ............ A61K/9/20 |
| EP | 0531611 | 4/1992 | ............ A61K/9/02 | WO | WO 9423698 | 10/1994 | ............ A61K/9/14 |
| EP | 0240904 | 7/1992 | ............ A61K/9/20 | WO | 9423700 | 10/1994 | ............ A61K/9/16 |
| EP | 0535841 | 9/1992 | ......... A61K/31/485 | WO | 9514460 | 6/1995 | ............ A61K/9/14 |
| EP | 0320480 | 11/1992 | ............. B01F/5/22 | | | | |
| EP | 0337256 | 11/1992 | ............ A61K/9/20 | | | | |
| EP | 0526862 | 2/1993 | ............ A61K/9/20 | | | | |
| EP | 0338383 | 3/1993 | ............ A61K/9/54 | | | | |
| EP | 0529396 | 3/1993 | ............ A61K/9/20 | | | | |
| EP | 0533297 | 3/1993 | ............ A61K/9/46 | | | | |
| EP | 0534628 | 3/1993 | ......... A61K/31/485 | | | | |
| EP | 0544144 | 6/1993 | ............ A61K/9/20 | | | | |
| EP | 0546676 | 6/1993 | .......... A61K/31/60 | | | | |
| EP | 0667065 | 8/1993 | ............ A61K/9/16 | | | | |
| EP | 665010 | 10/1993 | ............ A61K/9/26 | | | | |
| EP | 0574894 | 12/1993 | ......... A61K/31/575 | | | | |
| EP | 0580860 | 2/1994 | ............ A61K/9/14 | | | | |
| EP | 580860 | 2/1994 | | | | | |
| EP | 0582380 | 2/1994 | ............... B01J/2/16 | | | | |
| EP | 0624366 | 4/1994 | ......... A61K/31/135 | | | | |
| EP | 0595311 | 5/1994 | .......... A61K/31/44 | | | | |
| EP | 0249347 | 6/1994 | ......... A61K/31/485 | | | | |
| EP | 0436786 | 6/1994 | ........... B30B/11/22 | | | | |
| EP | 0636370 | 2/1995 | ......... A61K/31/485 | | | | |
| EP | 0491238 | 3/1995 | ............ B30B/11/22 | | | | |
| EP | 0642788 | 3/1995 | ......... A61K/31/135 | | | | |
| EP | 0609961 | 8/1995 | ......... A61K/31/485 | | | | |
| EP | 0205282 | 9/1995 | ............ A61K/9/22 | | | | |
| EP | 0624366 | 5/1996 | ......... A61K/31/135 | | | | |
| FR | 2273512 | 1/1976 | ............. A61J/3/06 | | | | |
| FR | 2273584 | 1/1976 | ............. B01J/2/10 | | | | |
| FR | 2642420 | 3/1990 | .......... C07C/55/10 | | | | |
| GB | 0997399 | 4/1964 | | | | | |

OTHER PUBLICATIONS

Frank W. Goodhart et al., Design and Use of a Laboratory Extruder for Pharmaceutical Granulations, Journal of Pharm. Scien., 62(1), pp. 133–136 (Jan. 1973).

Publication, KEX, Twin Screw Compounding Extruder, (Oct. 1989).

Abstract No. 2–223533 "Agent with Release–Controlled Matrix".

Derwent Abstract DE 2553026 (1976).

Derwent Abstract JP 62040277 (1987).

Derwent Abstract JP58109411 (1983).

Derwent Abstract EP 358 107 (1990).

Sekiguchi, et al., "Studies on Absorption of Eutectic Mixture . . . ", Chem. Pharm. Bull., vol. 9 (1961), pp. 866–872.

A.R. Gennaro, "Particle Phenomena and Coarse Dispersions", Remington's Pharmaceutical Sciences, 17th Edition, 1985, p. 301.

J.L. Ford, "The Current Status of Solid Dispersions", Pharm. Acta Helv. 61, Nr. 3 (1986), pp. 69–88.

CA 74:67660 (1996) (1 page).

CA 101:60081 (1996) (1 page).

CA 113:98975 (1996) (1 page).

CA 113:218240 (1996) (1 page).

CA 114:30199 (1996) (1 page).
CA 112:75438 (1996) (1 page).
CA 115:177364 (1997) (1 page).
R. Kinget, et al., "Preparation and Properties of Granulates Containing Solid Dispersions", Acta Phar. Tech., vol. 31, No. 2, 1985, pp. 57–62.
M.J. Jozwiakowski et al., "Characterization of a Hot–Melt Fluid Bed Coating Process for Fine Granules", Pharm. Research, vol. 7, No. 11, 1990, pp. 1119–1124.
B. Evrard et al., "Melt Granulation With a New Laboratory High–Shear Mixer", Laboratoire de Pharmacie Galenique, Institut de Pharmacie.
M. Niskanen et al., "Pelletization in a Centrifugal Granulator, Part I: Effects of Binder–Solution Concentration", Pharm. Tech. Int'l., Oct. 1990, pp. 22–38.
L. Lachman et al., "The Theory and Practice of Industrial Pharmacy", p. 315, Lea & Febiger, Phi. 1976.
FDA Guide to Inspections of Oral Solid Dosage Forms Pre/Post Approval Issues for Development and Validation, Jan. 1994.
T. Schaefer et al., "Melt Pelletization in a High Shear Mixer I Effects of Process Variables and Binder", Acta Pharm. Nord. vol. 4, No. 3, pp. 133–140, 1992.
T. Schaefer et al., "Melt Pelletization in a High Shear Mixer II Power Consumption and Granule Growth", Acta Pharm. Nord. vol. 4, No. 3, pp. 141–148, 1992.
T. Schaefer, et al., "Melt Granulation in a Laboratory Scale High Shear Mixer", Drug Dev. and Indust. Phar., vol. 16, No. 8, pp. 1249–1277, 1990.
McTaggart, C.M. et al., "The Evaluation of Formulation and Processing Conditions of a Melt Granulation Process", Int'L J. Pharm. vol. 19, No. 2, issued 1984, pp. 139–148.
El–Shanawany, S., "Sustained Release of Nitrofurantion From Inert Wax Matrixes", J. Controlled Release, vol. 26, No. 1, issued 1993, pp. 11–19.
P. Flanders, et al., "The Control of Drug Releases From Conventional Melt Granulation Matrices", Drug Dev. and Industrial Pharm., vol. 13, No. 6, pp. 1001–1022, 1987.
Thomsen, L. Juul, "Matrix Pellets Prolonged Formulations Prepared by Melt Pelletization", Dept. of Pharm. Royal Danish School of Pharmacy, 1992.
Thomsen,L., Juul, et al., "Prolonged Release Matrix Pellets Prepared by Melt Pelletization I. Process Variables", Drug Development and Industrial Pharmac y, vol. 19, No. 15, pp. 1867–1887 (1993).
Thomsen, L. Juul, et al., "Prolonged Release Matrix Pellets Prepared by Melt Pelletization II. Hydrophobic Substances as Meltable Binders", Drug Development and Industrial Pharmacy, vol. 20, No. 7, pp. 1179–1197 (1994).
Thomsen, L. Juul, "Utilizing melt pelletization tequnique for the preparation of prolonged release products", Pelletization, (material elaborated by assistant Prof. Lars Juul Thomsen, Dept. of Pharmaceutics, Royal Danish School of Pharmacy for the Die course "Pelletization Technology", Nov. 1992, 106 pages plus appendixes.
Thomsen, L. Juul, "Prolonged Release Matrix Pellets Prepared by Melt Pelletization. Part IV: Drug Content, Drug Particle Size and Binder Composition", Pharmaceutical Technology Europa, pp. 19–22 (Oct. 1994).
N. Follonier et al., "Evaluation of Hot–Melt Extrusion as a New Technique for the Production of Polymer–Based Pellets for Sustained Release Capsules Containing High Loadings of Freely Soluble Drugs", Drug. Dev. and Industr. Pharm., vol. 20, No. 8, pp. 1323–1339, (1994).

Sustained Release Medications, pp. 50–53, Noyes Data Crop. (J.C. Johnson), 1980.
M.A. Longer, "Sustained–Release Drug Deliver Systems", Remington's Pharm. Scie., 18th Edition, pp. 1676–1693, 1990.
M. Zahirul I. Khan, "Recent Trends and Progress in Sustained or Controlled Oral Delivery of Some Water Soluble Drugs: Morphine Salts, Diltiazem and Captopril", Drug Devl. and Industr. Pharm., vol. 21, No. 9, pp. 1037–1070, 1995.
J.P. Skelly, Scael–up of Immediate Release Oral Solid Dosage Forms, AAPS/FDA Workshop Committee, Pharmaceutical Technology, pp. 68–74, Apr. 1995.
SK Baveja et al., Int. J. Pharmaceutics, 41, (1988), pp. 55–62.
Formulating for Controlled Release with METHOCEL®Premium Cellulose Ethers, The Dow Chemical Company, 1989.
M.S. Vasquez et al., Ddrug Dev. & Ind. Pharmacy, 18 (11 & 12), pp. 1355–1378 (1992).
L W S Cheong et al., Pharm. Res. 9 (11), pp. 1510–1514 (1992).
Hunt et al., Clin. Ther., vol. 13, No. 4, pp. 482–488, 1990.
METHOCEL, Colorcon. Technical Information.
DA Alderman, Int. J. Pharm. Tech. and Prod. Mfr., 5(3), pp. 1–9, 1984.
HE Huber et al., J. Pharm. Sci. 55 (9), Sep. 1966, pp. 974–976.
Lin SY et al., Current Therapeutic Research 52 (3), pp. 486–492, Sep., 1992.
Aqualon Technical Information Bulletin, VC–585, 1991.
P. Colombo, Advanced Drug Delivery Reviews, 11 (1993), pp. 37–57.
KV Ranga Rao et al., Int. J. Pharmaceutics, 48 (1988), pp. 1–13.
JE Hogan, Drug Dev. & Ind. Pharmacy, 15 (6 & 7), pp. 975–999, (1989).
JL Ford et al., Int. J. Pharmaceutics, 24 (1985), pp. 327–338.
PB Daly et al., Int. J. Pharmaceutics, 18 (1984), pp. 201–205.
E.M.G. van Bommel, "Production and Evaluation of In Vitro Release Characteristics of Spherical Grandient Matrix Systems", Acta Phar., Technol. 3b (2), pp. 74–78, 1990.
Nicolas Follonier et al., "Various Ways of Modulating the Release of Diltiazem Hydrochloride from Hot–melt Extruded Sustained Release Pellets Prepard Using Polymeric Materials", Journal of Controlled Release, 36, pp. 243–250 (1995).
Alan Royce et al., "Alternative Granulation Technique: Melt Granulation", Drug Development and Industrial Pharmacy, 22 (9 & 10), pp. 917–992 (1996).
Derwent Abstract of EP 0208144, published Jan. 14, 1987.
English translation of Japanese text of J.L. White, *Twin Screw Extrusion, Technology and Principles*, pp. 14 and 37, 1981.

* cited by examiner

MELT-EXTRUSION MULTIPARTICULATES

This application is a continuation of Ser. No. 08/334,209 filed Nov. 4, 1994 now U.S. Pat. No. 5,965,161.

BACKGROUND OF THE INVENTION

The present invention relates to a process of making granulates or multiparticulates which are Useful, for example, in pharmaceutical dosage forms. In particular, the invention relates to a process for melt-extruding pharmaceutical agents with excipients to form multiparticulates suitable for inclusion in solid dosage forms such as capsules, tablets and the like.

It is known in the pharmaceutical art to prepare compositions which provide for controlled (slow) release of pharmacologically active substances contained in the compositions after oral administration to humans and animals. Such slow release compositions are used to delay absorption of a medicament until it has reached certain portions of the alimentary tract. Such sustained-release of a medicament in the alimentary tract further maintains a desired concentration of said medicament in the blood stream for a longer duration than would occur if conventional rapid release dosage forms are administered.

Over the years, several different methods of preparing controlled release pharmaceutical dosage forms have been suggested. For example, direct compression techniques, wet granulation techniques, encapsulation techniques and the like have been proposed to deliver pharmaceutically active ingredients to the alimentary tract over extended periods.

Melt granulation techniques have also been suggested to provide controlled release formulations. Melt granulation usually involves mechanically working an active ingredient in particulate form with one or more suitable binders and/or pharmaceutically acceptable excipients in a mixer until one or more of the binders melts and adheres to the surface of the particulate, eventually building up granules.

PCT International Publication No. WO 92/06679 discloses melt granulating methods for producing pellets containing therapeutically active substances. The method includes mechanically working a mixture containing the active substance in cohesive form with a binder having a melting point of 40–100° C., while supplying sufficient energy to melt the binder and form "overmoist" spherical pellets and thereafter adding an additional cohesive substance while maintaining the mechanical working to finally produce dry pellets.

PCT International Publication No. WO 93/18753 also discloses another melt extrusion process for preparing sustained-release pellets. This method includes pelletizing a mixture containing drug in finely divided form and a binder which includes one or more water-insoluble-wax-like binder substances with a melting point above 40° C. using a high shear mixer.

In the spite of the foregoing advances, a need for further alternatives in the field of controlled release formulations has been sought. The present invention addresses this need.

OBJECTS AND SUMMARY OF THE INVENTION

It is therefore an object of the present invention to provide improved methods for producing multiparticulates containing pharmaceutically active ingredients and excipients.

It is a further object of the present invention to provide multiparticulates containing pharmaceutically active ingredients which display improved controlled-release characteristics.

These objects and others have been accomplished by the present invention, which relates in part to a unit dose sustained-release oral dosage form containing a plurality of melt-extruded particles, each of said particles comprising:

a) a therapeutically active agent;
b) one or more retardants; and
c) an optional water-insoluble binder.

The particles have an average length of from about 0.1 to about 12 mm and the unit dose provides a release of the therapeutically active agent over at least about 8 hours.

Another aspect of the invention provides a method of preparing a multiparticulate sustained-release oral dosage form. This method includes mixing together a therapeutically effective agent, a water-insoluble retardant and an optional binder to form a homogeneous mixture, heating the mixture and thereafter extruding the mixture into strands. The strands are then cooled, and reduced to particles having a size of from about 0.1 to about 12 mm. This aspect further includes dividing the particles into unit doses. The ratio of water-insolube retardant material to therapeutically active agent is sufficient to impart a release of the active agent from the multiparticulate system over an extended time period. In this regard, the retardant will comprise about 5–95% of melt-extruded multi-particulate. The multiparticulate sustained-release system can be included within a hard gelatin capsule or other oral dosage forms such as a compressed tablet. Methods of preparing such dosage forms are also provided herein.

In yet a further aspect of the invention, there is provided a method of treating a patient with sustained-release multiparticulate formulations prepared as described above. This method includes administering a unit dose sustained release oral dosage form containing the novel melt-extruded particles to a patient in need of the active ingredient contained therein. For purposes of the present invention, a unit dose is understood to contain an effective amount of the therapeutically active agent.

A still further aspect of the invention provides an alternative method of preparing a multiparticulate sustained oral dosage form. This aspect includes directly metering into an extruder a homogeneous mixture of a water-insoluble retardant, a therapeutically active agent, and an optional binder, heating the homogeneous mixture, extruding said mixture to form strands, cooling the strands and cutting the strands into particles having a size of from about 0.1 to 12 mm and dividing the particles into unit doses. The ratio of hydrophobic material, namely water-insoluble retardant (and optional binder) to the therapeutically active agent is sufficient to impart a controlled release of the therapeutically active agent from the melt-extruded particles and unit doses over a time period of at least 8 hours.

BRIEF DESCRIPTION OF THE DRAWINGS

The following drawings are illustrative of embodiments of the invention and are not meant to limit the scope of the invention as encompassed by the claims.

FIG. 4 is a graph displaying the dissolution results of Examples 7 and 8;

DETAILED DESCRIPTION

Figure 1:
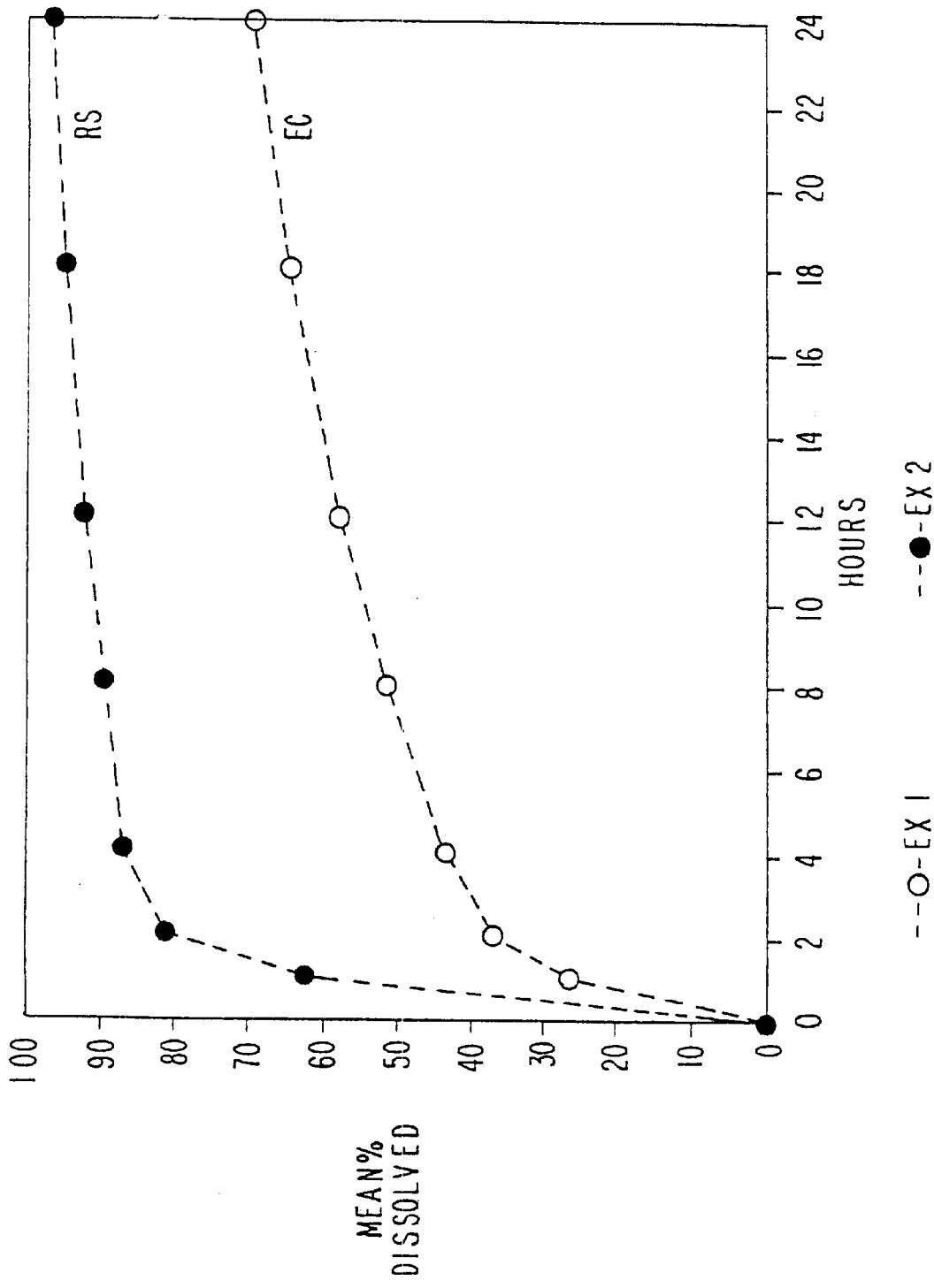
FIG. 1 is a graph displaying the dissolution results of Examples 1 and 2.
Figure 2:
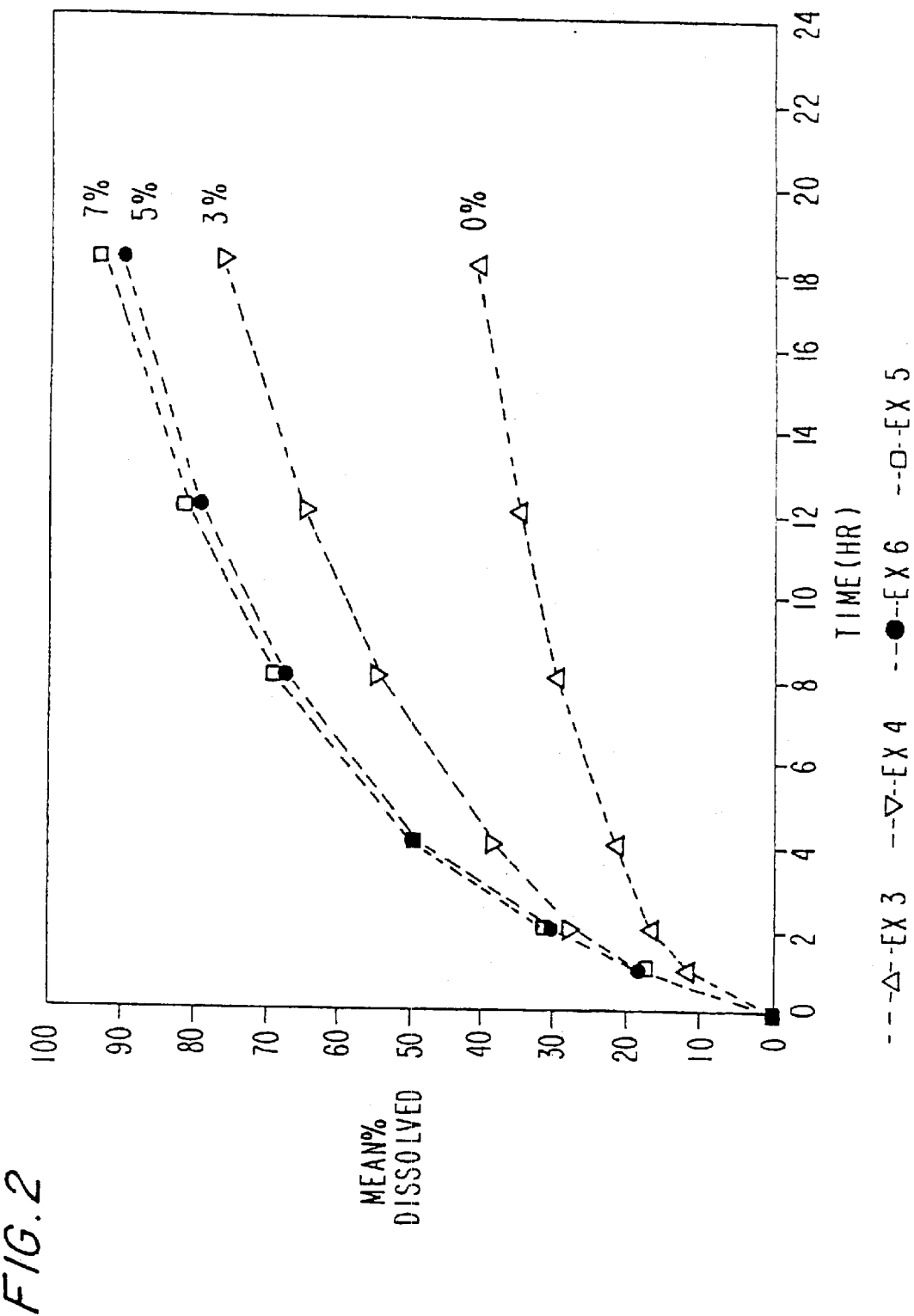
FIG. 2 is a graph displaying the dissolution rates of Examples 3–6.

In accordance with the present invention, there are provided methods for preparing multiparticulates using melt-extrusion techniques and sustained release oral unit dosage forms containing a plurality of the melt extruded particulates. In accordance therewith, a therapeutically active agent is combined with one or more suitable controlled-release retardants, and optionally, a water-insoluble binder, extruded and thereafter rendered into a plurality of melt-extruded particles or multiparticulates, such as spheres, beads or the like.

Pharmaceutical Agents

The active pharmaceutical agent (s) included in the controlled release multiparticulates of the present invention include systemically active therapeutic agents, locally active therapeutic agents, disinfecting agents, chemical impregnants, cleansing agents, deodorants, fragrances, dyes, animal repellents, insect repellents, a fertilizing agents, pesticides, herbicides, fungicides, and plant growth stimulants, and the like. The only limitation on the ingredient is that the pharmaceutical agent is capable of undergoing the inventive extrusion process without substantially losing its sought-after effect.

A wide variety of therapeutically active agents can be used in conjunction with the present invention. The therapeutically active agents (e.g. pharmaceutical agents) which may be used in the compositions of the present invention include both water soluble and water insoluble drugs. Examples of such therapeutically active agents include antihistamines (e.g., dimenhydrinate, diphenhydramine, chlorpheniramine and dexchlorpheniramine maleate), analgesics (e.g., aspirin, codeine, morphine, dihydromorphone, oxycodone, etc.), non-steroidal anti-inflammatory agents (e.g., naproxyn, diclofenac, indomethacin, ibuprofen, sulindac), anti-emetics (e.g., metoclopramide), anti-epileptics (e.g., phenytoin, meprobamate and nitrezepam), vasodilators (e.g., nifedipine, papaverine, diltiazem and nicardirine), anti-tussive agents and expectorants (e.g., codeine phosphate), anti-asthmatics (e.g. theophylline), antacids, anti-spasmodics (e.g. atropine, scopolamine), antidiabetics (e.g., insulin), diuretics (e.g., ethacrynic acid, bendrofluazide), anti-hypotensives (e.g., propranolol, clonidine), antihypertensives (e.g, clonidine, methyldopa), bronchodilators (e.g., albuterol), steroids (e.g., hydrocortisone, triamcinolone, prednisone), antibiotics (e.g., tetracycline), antihemorrhoidals, hypnotics, psychotropics; antidiarrheals, mucolytics, sedatives, decongestants, laxatives, vitamins, stimulants (including appetite suppressants such as phenylpropanolamine), as well as salts, hydrates, and solvates of the same. The above list is not meant to be exclusive.

In certain preferred embodiments, the multiparticulate systems of the present invention include one or more compounds known as opioid analgesics. Opioid analgesic compounds which may be used in the present invention include alfentanil, allylprodine, alphaprodine, anileridine, benzylmorphine, bezitramide, buprenorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levallorphan, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene, sufentanil, tramadol, tilidine, salts thereof, mixtures of any of the foregoing, mixed mu-agonists/antagonists, mu-antagonist combinations, and the like.

In certain particularly preferred embodiments, the opioid analgesic is selected from morphine, codeine, hydromorphine, hydrocodone, oxycodone, dihydrocodeine, dihydromorphine, oxymorphone, hydrates and solvates of any of the foregoing, mixtures of any of the foregoing, and the like.

Controlled Release Retardants and Binders

According to the present invention, in order to obtain a controlled release of the active agent, the therapeutically active agent is homogeneously combined with a sufficient amount of a release-retardant material and, optionally, a water-insoluble binder prior to undergoing extrusion. The retardant can be a hydrophobic material such as a water-insoluble acrylic polymer or alkylcellulose, or a water soluble material such as hydroxyalkylcelluloses and related materials. If unit doses of the multiparticulate are to have about a 12 hour or shorter release pattern, hydroxyalkylcelluloses, for example will be extruded with the therapeutic agent. If release rates of greater than about 12 hours are desired, water-insoluble materials are selected. It is, of course, within the scope of the invention to have particles containing mixtures of the water soluble and insoluble polymers.

In certain preferred embodiments of the present invention, the hydrophobic polymer is a pharmaceutically acceptable acrylic polymer, including but not limited to acrylic acid and methacrylic acid copolymers, methyl methacrylate copolymers, ethoxyethyl methacrylates, cynaoethyl methacrylate, aminoalkyl methacrylate copolymer, poly (acrylic acid), poly(methacrylic acid), methacrylic acid alkylamide copolymer, poly(methyl methacrylate), poly (methacrylic acid) (anhydride), methyl methacrylate, polymethacrylate, poly(methyl methacrylate), poly(methyl methacrylate) copolymer, polyacrylamide, aminoalkyl methacrylate copolymer, poly(methacrylic acid anhydride), and glycidyl methacrylate copolymers.

The melt-extruded particle will comprise from about 1 to about 99% by weight of the retardant and preferably from about 5 to 95% by weight. Other retardant polymers which may be used for the extrusion process of the present invention, as those skilled in the art will appreciate, include other cellulosic polymers, including other alkyl cellulosic polymers, may be substituted for part or all of water-insoluble portion of the retardant in the multiparticulate.

The terms "sustained release" and "extended duration" are defined for purposes of the present invention as the release of the drug (i.e., opioid analgesic) at such a rate that blood (e.g., plasma) levels are maintained within the therapeutic range but below toxic levels over a period of time greater than 6 hours, more preferably for periods of up to about 24 hours, or longer.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the Tradename Eudragit®. In further preferred embodiments, the acrylic polymer comprises a mixture of two acrylic resin lacquers commercially available from Rohm Pharma under the Tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® and Eudragit®L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit® RL and 50% Eudragit® RS, and 10% Eudragit® RL:Eudragit® 90% RS. Of course, one skilled in the art will recognize that other acrylic polymers may also be used, such as, for example, Eudragit® L.

In other preferred embodiments, the hydrophobic polymer which may be used is a hydrophobic cellulosic material such as ethylcellulose. Those skilled in the art will appreciate that other cellulosic polymers, including other alkyl cellulosic polymers, may be substituted for part or all of the ethylcellulose included in the hydrophobic polymer portion of the multiparticulates of the present invention.

In certain preferred embodiments, the release-modifying agent or retardant is selected from materials such as hydroxyalkylcelluloses such as hydroxypropylmethylcellulose and mixtures of the foregoing.

The retardants may also include a plasticizer. Examples of suitable plasticizers for ethylcellulose include water insoluble plasticizers such as dibutyl sebacate, diethyl phthalate, triethyl citrate, tributyl. citrate, and triacetin, although it is possible that other water-insoluble plasticizers (such as acetylated monoglycerides, phthalate esters, castor oil, etc.) may be used. Triethyl citrate is especially preferred.

Examples of suitable plasticizers for the acrylic polymers of the present invention include citric acid esters such as triethyl citrate NF XVI, tributyl citrate, dibutyl phthalate, and possibly 1,2-propylene glycol, polyethylene glycols, propylene glycol, diethyl phthalate, castor oil, and triacetin, although it is possible that other water-insoluble plasticizers (such as acetylated monoglycerides, phthalate esters, castor oil, etc.) may be used. Triethyl citrate is especially preferred.

The binder portion of the melt-extruded particles is optionally included. It has been found that the binder can be reduced or even eliminated from the extrusion if the physical properties and relationships between the therapeutically active ingredient and retardant(s) allow a sufficiently cohesive extruded strand to exit the apparatus. A non-limiting list of suitable binders includes hydrogenated vegetable or castor oil, paraffin, higher aliphatic alcohols, higher aliphatc acids, long chain fatty acids, fatty acid esters, and mixtures thereof.

The binder material may consist of one or more water-insoluble wax-like thermoplastic substances possibly mixed with one or more wax-like thermoplastic substances being less hydrophobic than said one or more water-insoluble wax-like substances. In order to achieve constant release, the individual wax-like substances in the binder material should be substantially non-degradable and insoluble in gastrointestinal fluids during the initial release phases.

Useful water-insoluble wax-like substances may be those with a water-solubility that is lower than about 1:5,000 (w/w).

Binder materials are preferably water-insoluble with more or less pronounced hydrophilic and/or hydrophobic trends. Specifically, the wax-like substance may comprise fatty alcohols, fatty acid esters, fatty acid glycerides (mono-, di-, and tri-glycerides), hydrogenated fats, hydrocarbons, normal waxes, stearic aid, stearyl alcohol and hydrophobic and hydrophilic polymers having hydrocarbon backbones.

In addition to the foregoing, the melt-extruded particles can be prepared to include pharmaceutically acceptable carriers and excipients. It is to be understood that these materials can be mixed with the particles after extrusion as well. Specific examples of pharmaceutically acceptable carriers and excipients that may be used to formulate oral dosage forms are described in the *Handbook of Pharmaceutical Excipients*, American Pharmaceutical Association (1986), incorporated by reference herein. Techniques and compositions for making solid oral dosage forms are described in *Pharmaceutical Dosage Forms: Tablets* (Lieberman, Lachman and Schwartz, editors) Second Edition, published by Marcel Dekker, Inc., incorporated by reference herein. Techniques and compositions for making tablets (compressed and molded), capsules (hard and soft gelatin) and pills are also described in *Remington's Pharmaceutical Sciences*, (Arthur Osol, editor), 1553–1593 (1980), incorporated by reference herein.

An optional process for preparing the multiparticulates and unit doses of the present invention includes directly metering into an extruder a water-insoluble retardant, a therapeutically active agent, and an optional binder; heating said homogenous mixture; extruding said homogenous mixture to thereby form strands; cooling said strands containing said homogeneous mixture; and cutting said strands into particles having a size from about 0.1 mm to about 12 mm; and dividing said particles into unit doses. In this aspect of the invention, a relatively continuous manufacturing procedure is realized.

Multiparticulates and Multiparticulate Systems

The multiparticulate system can be, for example, in the form of granules, spheroids or pellets depending upon the extruder exit orifice. For purposes of the present invention, the terms "multiparticulate(s)" and "multiparticulate system (s)" and "melt-extruded paricles" shall refer to a plurality of units, preferably within a range of similar size and/or shape and containing one or more active agents and one or more excipients, preferably including a retardant as described herein. In this regard, the multiparticulates will be of a range of from about 0.1 to about 12 mm in length and have a diameter of from about 0.1 to about 5 mm. In addition, it is to be understood that the multiparticulates can be any geometrical shape within this size range such as beads, microspheres, seeds, pellets, etc.

The multiparticulate can thereafter be included in a capsule or in any other suitable solid form.

The term "unit dose" is defined for purposes of the present invention as the total amount of substrates needed to administer a desired dose of drug (e.g., opioid analgesic) to a patient.

In one especially preferred embodiment, oral dosage forms are prepared to include an effective amount of multiparticulates within a capsule. For example, a plurality of the melt extruded particles may be placed in a gelatin capsule in an amount sufficient to provide an effective controlled-release dose when ingested and contacted by gastric fluid. In certain preferred embodiments of the present invention, the sustained-release multiparticulate systems are coated with a sustained-release coating. The coating formulations of the present invention should be capable of producing a strong, continuous film that is smooth and elegant, capable of supporting pigments and other coating additives, non-toxic, inert, and tack-free.

In order to obtain a sustained-release of opioid, for example, sufficient to provide an analgesic effect for the extended durations set forth in the present invention, the melt extruded particles comprising the therapeutically active agent may be coated with a sufficient amount of hydrophobic material to obtain a weight gain level from about 2 to about 30 percent, although the overcoat may be greater depending upon the physical properties of the particular opioid analgesic compound utilized and the desired release rate, among other things. In certain preferred embodiments of the present invention, the hydrophobic polymer comprising the sustained-release coating is a pharmaceutically acceptable acrylic polymer, such as those described hereinabove.

The solvent which is used for the hydrophobic material may be any pharmaceutically acceptable solvent, including water, methanol, ethanol, methylene chloride and mixtures thereof. It is preferable however, that the coatings be based upon aqueous dispersions of the hydrophobic material.

In one preferred embodiment the multiparticulate is used in a sustained-release opioid oral dosage form and includes hydromorphone as the therapeutically active ingredient in an amount from about 4 to about 64 mg hydromorphone hydrochloride. Alternatively, the dosage form may contain molar equivalent amounts of other hydromorphone salts or of the hydromorphone base. In other preferred embodiments where the opioid analgesic is other than hydromorphone, the dosage form contains an appropriate amount to provide a substantially equivalent therapeutic effect. For example, when the opioid analgesic comprises morphine, the sustained-release oral dosage forms of the present invention include form about 5 mg to about 800 mg morphine, by weight. When the opioid analgesic comprises oxycodone, the sustained-release oral dosage forms of the present invention include from about 5 mg to about 400 mg oxycodone. In these aspects of the invention, the multiparticulate can be encapsulated or compressed into solid oral dosage forms further include combinations of multiparticulates containing one or more of the active agents disclosed above before being encapsulated. Furthermore, the unit dosage forms can also include an amount of an immediate release active agent for prompt therapeutic effect.

The controlled-release formulations of the present invention slowly release the therapeutically active agent, e.g., when ingested and exposed to gastric fluids, and then to intestinal fluids. The controlled-release profile of the formulations of the invention can be altered, for example, by varying the amount of retardant, i.e., hydrophobic polymer, by varying the amount of plasticizer relative to hydrophobic polymer, by the inclusion of additional ingredients or excipients, by altering the method of manufacture, etc.

For example, hydromorphone-containing multiparticulate may also be overcoated with an aqueous dispersion of the hydrophobic polymer. The aqueous dispersion of hydrophobic polymer preferably further includes an effective amount of plasticizer, e.g. triethyl citrate. Pre-formulated aqueous dispersions of ethylcellulose, such as Aquacoat® or Surelease®, may be used. If Surelease® is used, it is not necessary to separately add a plasticizer. Alternatively, pre-formulated aqueous dispersions of acrylic polymers such as Eudragit® can be used. These coating solutions may also contain film-formers, plasticizers, a solvent system (i.e., water), a colorant to provide elegance and product distinction. Color may also be added to or during the extrusion of the therapeutically active agent and retardant.

The plasticized aqueous dispersion of hydrophobic polymer may be applied onto the multiparticulate comprising the therapeutically active agent by spraying using any suitable spray equipment known in the art. In a preferred method, a Wurster fluidized-bed system is used in which an air jet, injected from underneath, fluidizes the multiparticulate material and effects drying while the acrylic polymer coating is sprayed on. A sufficient amount of the aqueous dispersion of hydrophobic polymer to obtain a predetermined controlled-release of said therapeutically active agent when the coated particulate is exposed to aqueous solutions, e.g. gastric fluid, is preferably applied, taking into account the physical characteristics of the therapeutically active agent, the manner of incorporation of the plasticizer, etc.

In addition to the above ingredients, a controlled-release matrix may also contain suitable quantities of other materials, e.g. diluents, lubricants, binders, granulating aids, colorants, flavorants and glidants that are conventional in the pharmaceutical art in amounts up to about 50% by weight of the particulate if desired.

In a further aspect of the present invention, a process for the preparation of a multiparticulate controlled release, oral dosage form is provided, This aspect includes homogeneously mixing a therapeutically effective agent with a water-insoluble retardant and, optionally, a binder; extruding the mixture, cooling the exiting extruded strands, rendering the strands into particles having a size of from about 0.1 to about 12 mm in length and optionally, encapsulating or compressing and shaping the granules into tablets. The diameter of the extruder aperture or exit port can also be adjusted to vary the thickness of the extruded strands. Furthermore, the exit part of the extruder need not be round; it can be oblong, rectangular, etc. The exiting strands can be reduced to particles using a hot wire cutter, guillotine, etc.

DETAILED DESCRIPTION OF THE PREFERRED EMBODIMENTS

Figure 9:
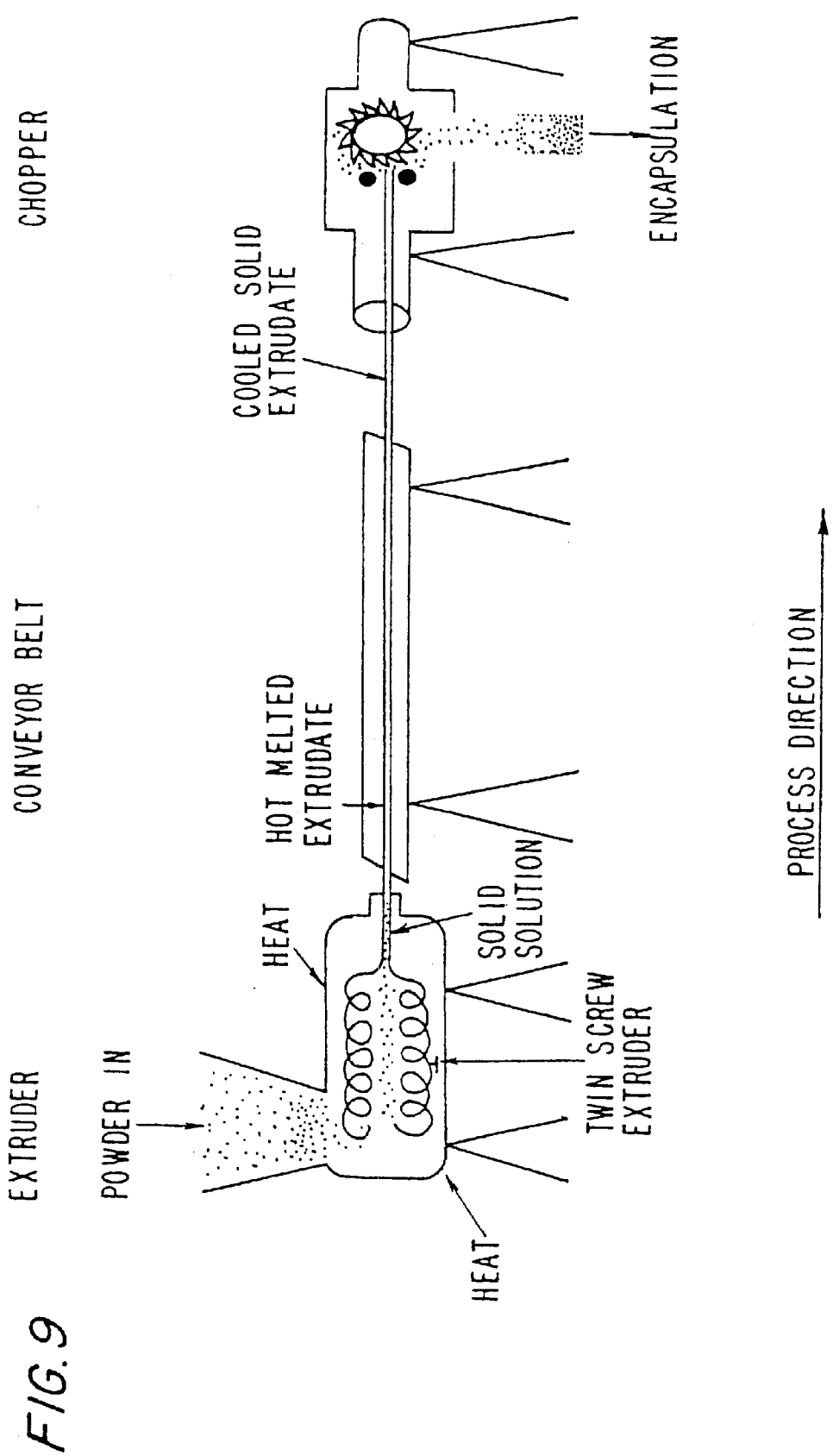
FIG. 9 is a schematic representation of a system for carrying out the present invention.

As shown in FIG. 9, a typical melt extrusion systems capable of carrying out the present invention include a suitable extruder drive motor having variable speed and constant torque control, start-stop controls, and ammeter. In addition, the system will include a temperature control console which includes temperature sensors, cooling means and temperature indicators throughout the length of the extruder. In addition, the system will include an extruder such as twin-screw extruder which consists of two counter-rotating intermeshing screws enclosed within a cyclinder or barrel having an aperture or die at the exit thereof. The feed materials enter through a feed hopper and is moved through the barrel by the screws and is forced through the die into strands which are thereafter conveyed such as by a continuous movable belt to allow for cooling and being directed to a pelletizer or other suitable device to render the extruded ropes into the multiparticulate system. The pelletizer can consist of rollers, fixed knife, rotating cutter and the like. Suitable instruments and systems are available from distributors such as C. W. Brabender Instruments, Inc. of South Hackensack, N.J. Other suitable apparatus will be apparent to those of ordinary skill in the art.

General Pellet Manufacturing Procedure

Premix the required amount of drug, polymers, and optional binder (wax).

Charge a powder feeder with proper amount of drug/excipient blend.

Set temperatures of extruder to the required temperature, depending on the formulation. Wait until the corresponding heating zones reach steady temperatures. Start the feeder and the extruder. The drug/excipient powder blend is melted and intimately mixed in the extruder. The diameter of the extruder aperture can be adjusted to vary the thickness of the resulting strand.

Set the conveyor belt speed to an appropriate speed (e.g., 3–100 ft/min). Allow the extruded semisolid strand(s) to be congealed and transported to the pelletizer. Additional cooling devices may be needed to ensure proper congealing. (The conveyor belt may not be needed to cool the strand, if the material congeals rapidly enough.)

Set the roller speed and cutter speed (e.g., to 3–100 ft/min and 100–800 rpm). Cut the congealed strands to desired size (e.g., 3–5 mm in diameter, 0.3–5 mm in length).

Collect the pellet product.

Fill a desired weight of pellets into hard gelatin capsules to obtain. an appropriate does of the drug.

Dissolution Method (USP II Paddle at 100 rpm) 1st hour in 700 ml simulated gastric fluid or SGF thereafter, 900 ml simulated intestinal fluid SIF Using HPLC procedures for assay The following examples illustrate various aspects of the present invention. They are not meant to be construed to limit the claims in any manner whatsoever.

EXAMPLES 1–2

In these examples, chlorpheniramine maleate controlled release pellets were prepared according to the above manufacturing procedure using ethylcellulose and an acrylic polymer (Eudragit RSPO), respectively as the retardant. The formulations are set forth in Tables 1 and 2 below. The dissolution of these formulations is set forth in FIG. 1. Drug release rate from ethylcellulose pellets (prepared at 105° C.) is significantly slower than that from Eudragit RS pellets (prepared at 85° C).

TABLE 1

EX. 1

| Composition | Amt. (mg) per Capsule |
| --- | --- |
| Chlorpheniramine Maleate | 60 |
| Ethyl Cellulose | 84 |
| Stearic Acid | 36 |
| Total | 180 |

TABLE 2

EX. 2

| Composition | Amt. (mg) per Capsule |
| --- | --- |
| Chlorpheniramine Maleate | 60 |
| Eudragit RSPO | 84 |
| Stearic Acid | 36 |
| Total | 180 |

EXAMPLES 3–6

Ex. 3

The excipients used in Ex. 2 were employed to make morphine sulfate controlled release pellets. The drug release rate was slower than expected especially during later hours of the dissolution.

Ex. 4–6

To increase the drug dissolution rate during later hours, varying amounts of Eudragit L-100 were incorporated in the formulation. The drug dissolution rate increases with increasing amount of Eudragit L-100 in the formulation.

TABLE 3

EX. 3

| Composition | Amt. (mg) per Capsule |
| --- | --- |
| Morphine Sulfate | 60 |
| Eudragit RSPO | 42 |
| Stearic Acid | 18 |
| Total | 120 |

TABLE 4

EX. 4.

| Composition | Amt. (mg) per Capsule |
| --- | --- |
| Morphine Sulfate | 60 |
| Eudragit RSPO | 38.4 |
| Eudragit L-100 | 3.6 |
| Stearic Acid | 18 |
| Total | 120 |

TABLE 5

EX. 5

| Composition | Amt. (mg) per Capsule |
|---|---|
| Morphine Sulfate | 60 |
| Eudragit RSPO | 36 |
| Eudragit L-100 | 6 |
| Stearic Acid | 18 |
| Total | 120 |

TABLE 6

EX. 6

| Composition | Amt. (mg) per capsule |
|---|---|
| Morphine Sulfate | 60 |
| Eudragit RSPO | 33.6 |
| Eudragit L-100 | 8.4 |
| Stearic Acid (SA) | 18 |
| Total | 120 |

Figure 3:
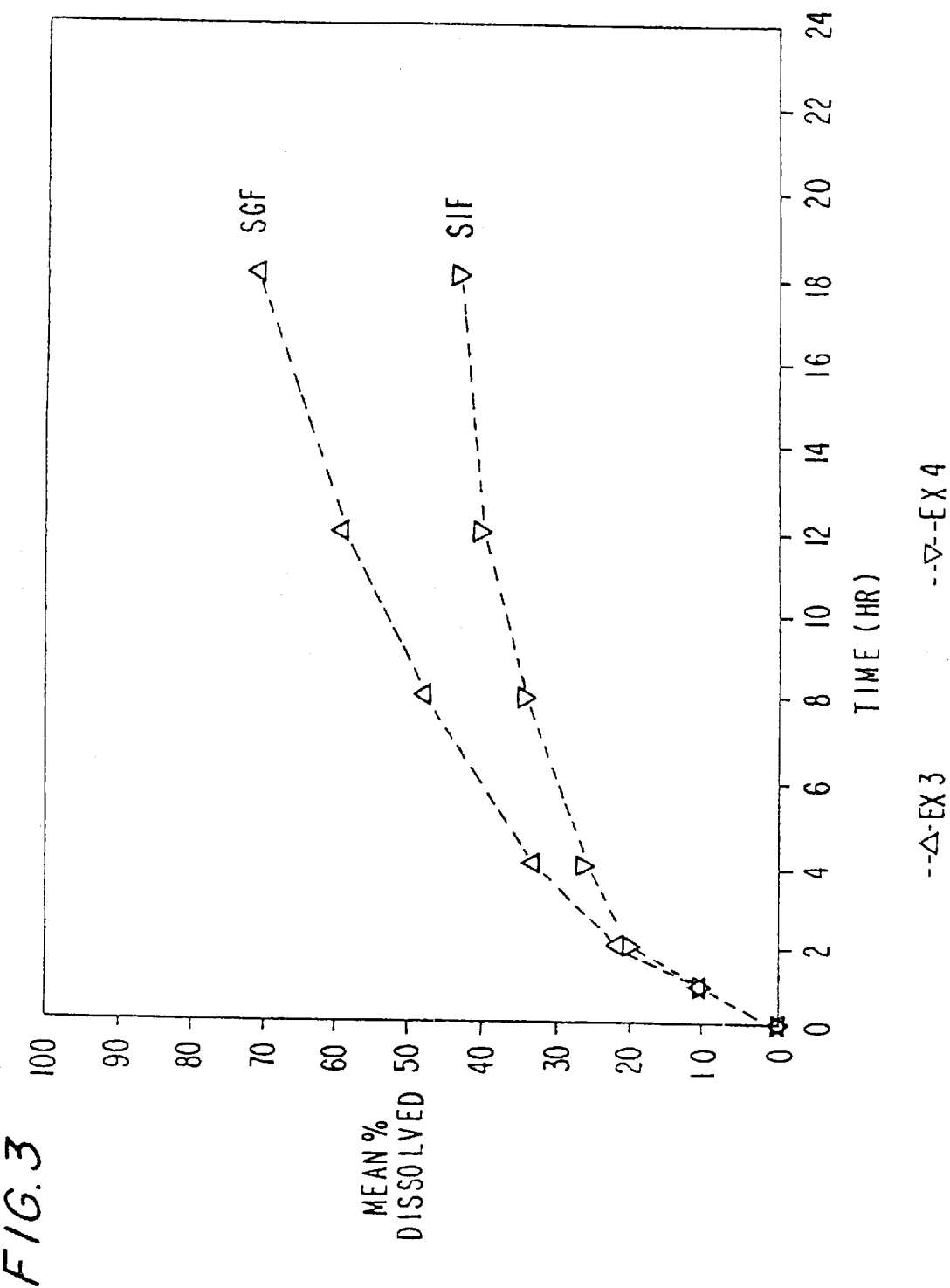
FIGS. 3 and 4 are graphs displaying the pH dependency of the dissolution results of Examples 3, 4 and 6 respectively.

As seen in FIG. 3, the drug dissolution rate obtained from the product of Ex. 3 showed a significant pH dependency. The release rate was slower in SIF (simulated intestinal fluid) than in SGF (simulated gastric fluid).

Figure 4:
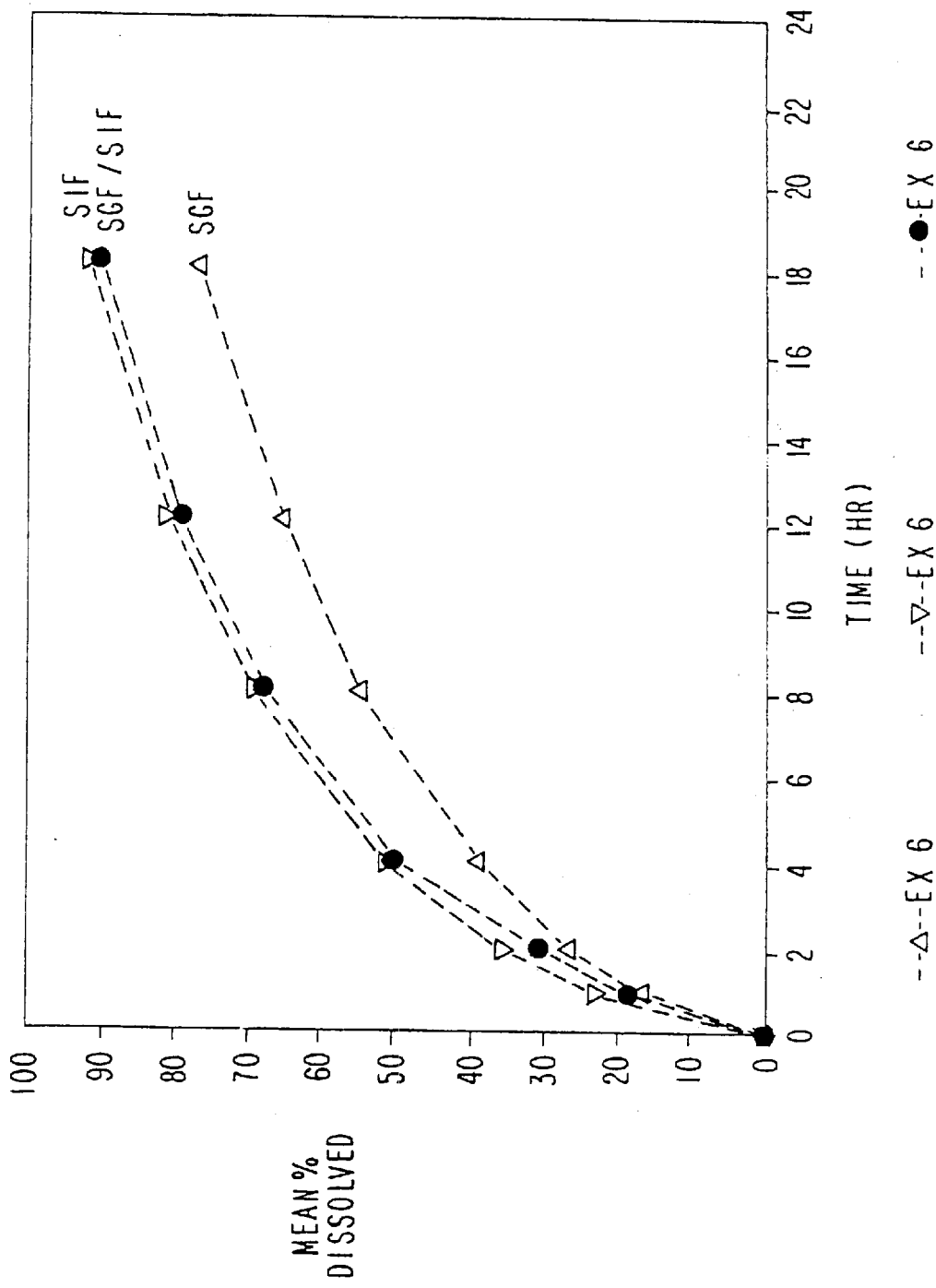

In FIG. 4, it can be seen that due to the addition of Eudragit L-100, the drug dissolution rate obtained from Ex. 6 was less pH dependent. The drug release rate was faster in SIF during later hours of dissolution which is desirable for complete bioavailability.

EXAMPLES 7–8

Figure 5:
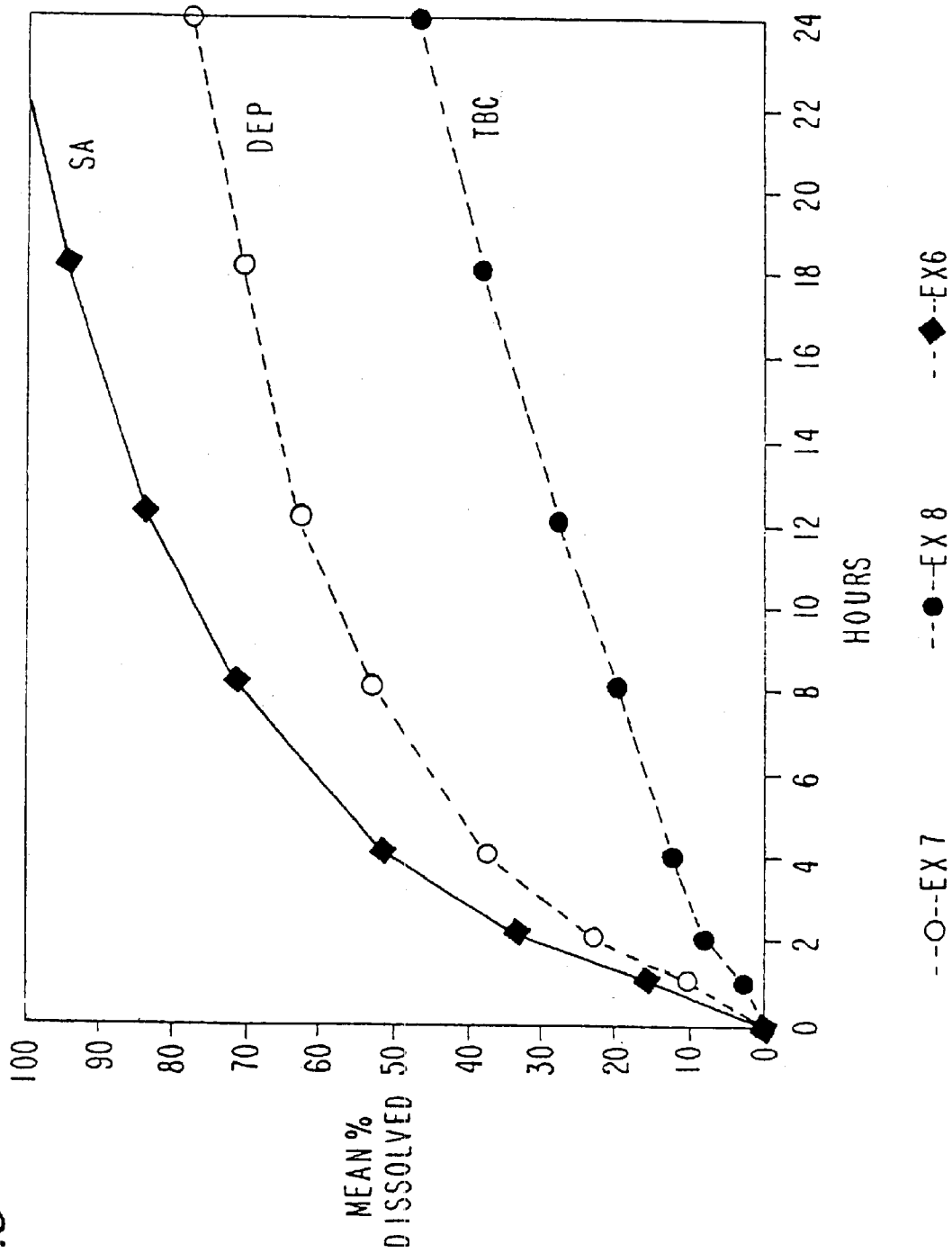
FIG. 5 is a graph displaying the dissolution results of Examples 6, 7 and 8.

As demonstrated in FIG. 5, with proper choice of plasticizers, the drug release rate from the formula containing Eudragit L-100 can be reduced. This may be necessary to achieve desirable plasma drug concentration profiles after oral administration of the pellets.

TABLE 7

EX. 7

| Composition | Amt. (mg) per Capsule |
|---|---|
| Morphine Sulfate | 60 |
| Eudragit RSPO | 33.6 |
| Eudragit L-100 | 8.4 |
| Stearic Acid (SA) | 9 |
| Diethyl Phthalate (DEP) | 9 |
| Total | 120 |

TABLE 8

EX. 8

| Composition | Amt. (mg) per Capsule |
|---|---|
| Morphine Sulfate | 60 |
| Eudragit RSPO | 33.6 |
| Eudragit L-100 | 8.4 |
| Stearic Acid (SA) | 9 |
| Tributyl Citrate (TBC) | 9 |
| Total | 120 |

EXAMPLES 9–10

Figure 6:
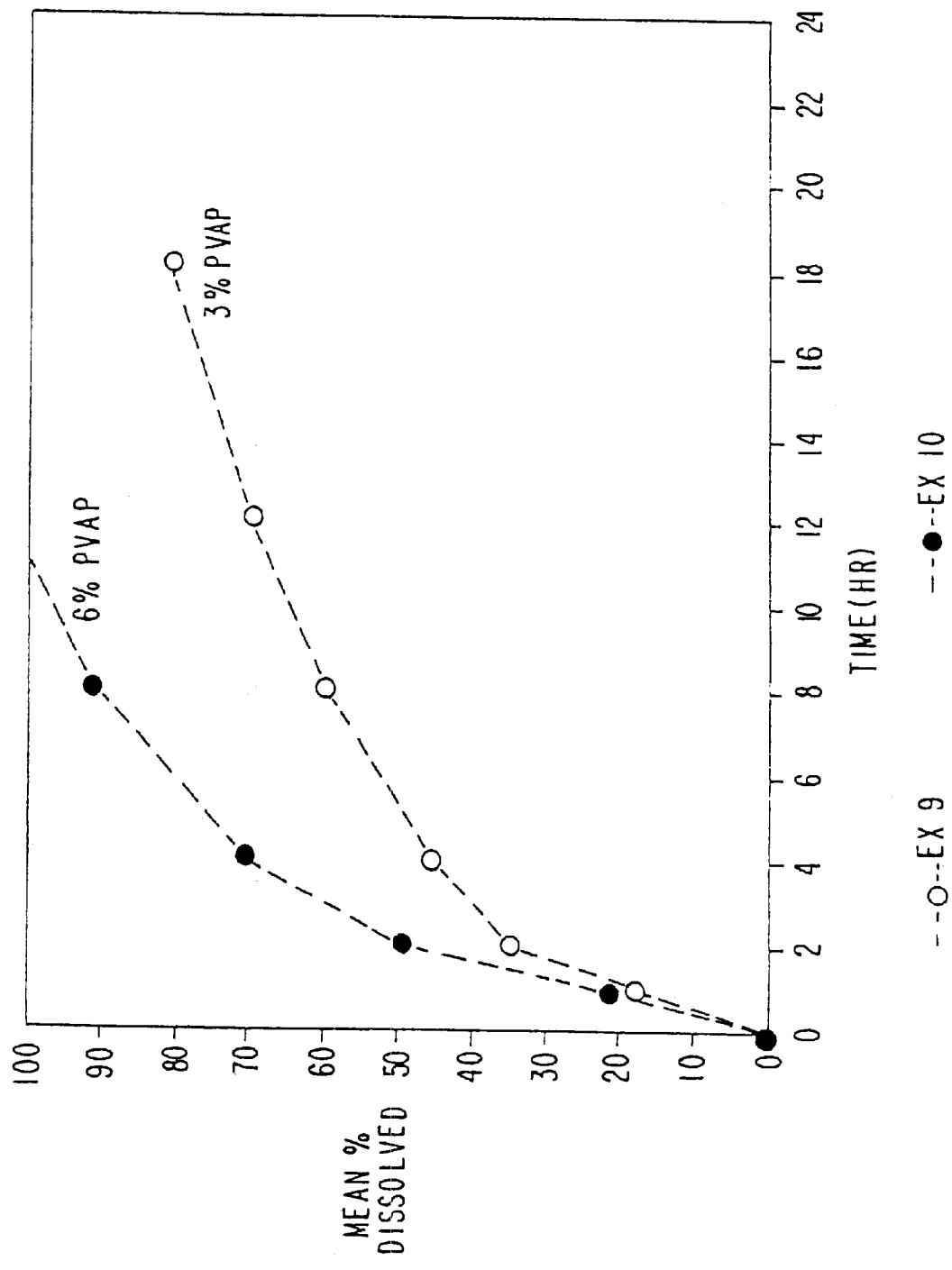
FIG. 6 is a graph displaying the dissolution results of Examples 9 and 10.

A different polymer/wax combination was used as an alternative formulation. As seen in FIG. 6, the drug dissolution rate from ethylcellulose/polyvinyl acetate phthalate was somewhat faster.

TABLE 9

EX. 9

| Composition | Amt. (mg) per Capsule |
|---|---|
| Morphine Sulfate | 60 |
| Ethyl Cellulose | 38.4 |
| Polyvinyl Acetate Phthalate | 3.6 |
| Stearic Acid | 18 |
| Total | 120 |

TABLE 10

EX. 10

| Composition | Amt. (mg) per Capsule |
|---|---|
| Morphine Sulfate | 60 |
| Ethyl Cellulose | 34.8 |
| Polyvinyl Acetate Phthalate | 7.2 |
| Stearic Acid | 18 |
| Total | 120 |

EXAMPLES 11–12

Figure 7:
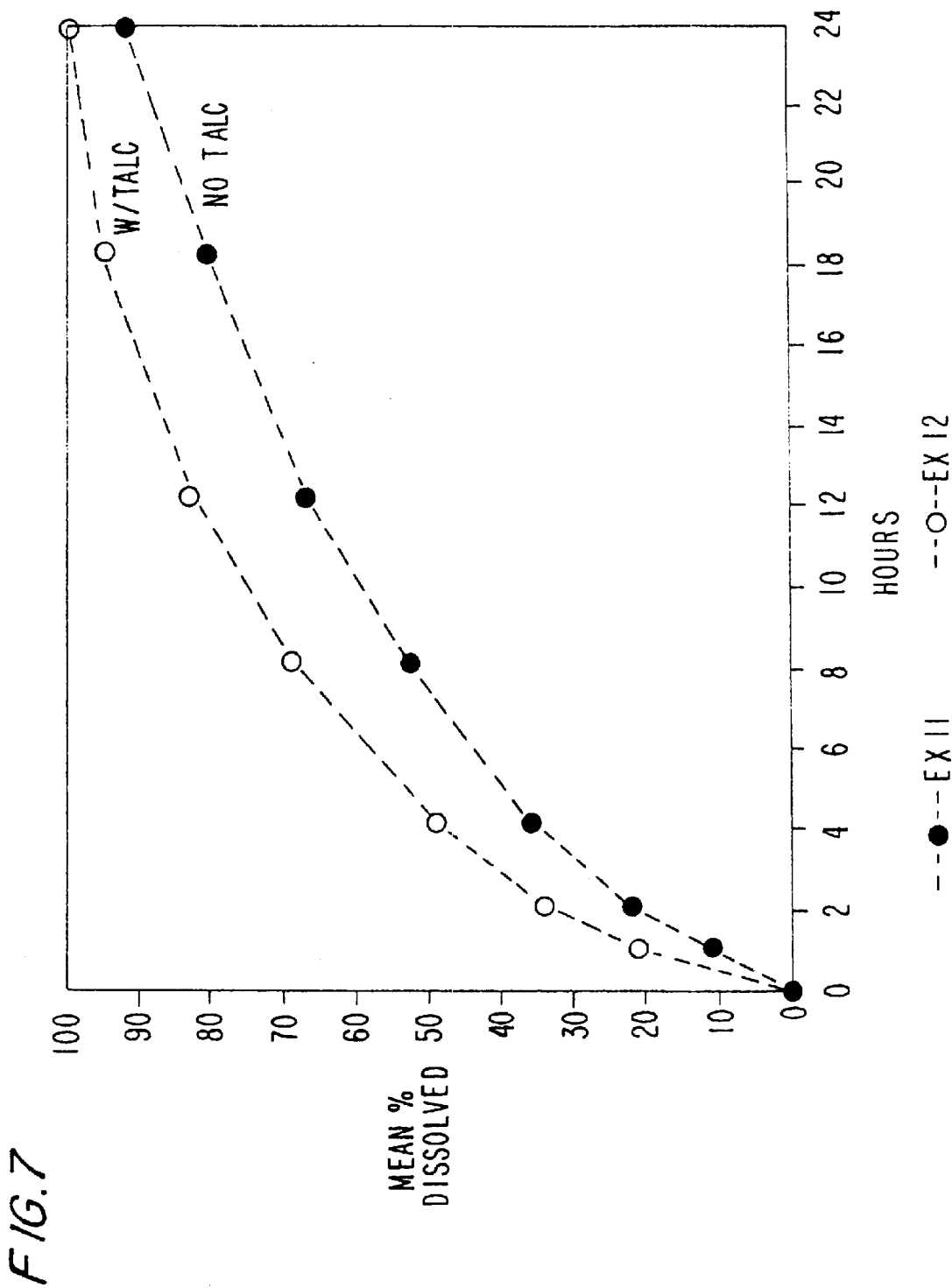
FIG. 7 is a graph displaying the dissolution results of Examples 11 and 12.

The formula used in Ex. 5 was applied to oxycodone hydrochloride. Due to the higher potency of oxycodone, only 20 mg of drug was used. The missing 40 mg was replaced by 40 mg of talc (Ex. 12). No replacement was used in Ex. 11. When tested in only SGF or SIF, the use of Eudragit L causes the formulation to become less pH dependent. The results are shown in FIG. 7.

TABLE 11

EX. 11

| Composition | Amt. (mg) per Capsule |
|---|---|
| Oxycodone Hydrochloride | 20 |
| Eudragit RSPO | 36 |
| Eudragit L-100 | 6 |
| Stearic Acid | 18 |
| Total | 120 |

TABLE 12

EX. 12

| Composition | Amt. (mg) per Capsule |
|---|---|
| Oxycodone Hydrochloride | 20 |
| Eudragit RSPO | 36 |
| Eudragit L-100 | 6 |
| Stearic Acid | 18 |
| Talc | 40 |
| Total | 120 |

EXAMPLES 13–14

Hydromorphone

Figure 8:
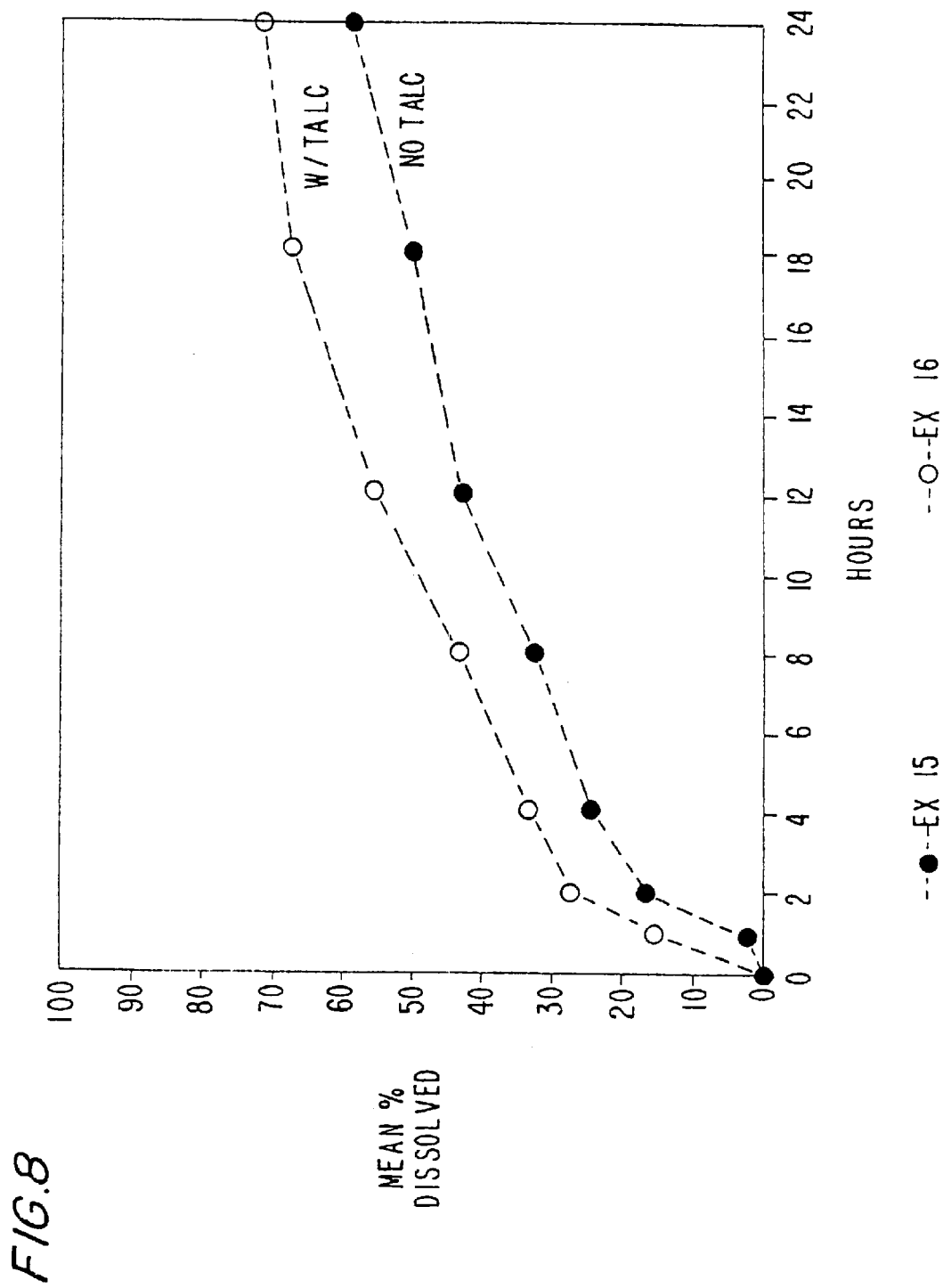
FIG. 8 is a graph displaying the dissolution results of Examples 15 and 16.

The formula used in Ex. 5 was applied to hydromorphone hydrochloride. Due to the higher potency of hydromorphone, only 8 mg of drug was used. The missing 52 mg was replaced by 52 mg of talc (Ex. 14) or 52 mg of excipients (Ex. 13). The results are shown in FIG. 8.

TABLE 13

EX. 13

| Composition | Amt. (mg) per Capsule |
|---|---|
| Hydromorphone Hydrochloride | 8 |
| Eudragit RSPO | 67.2 |
| Eudragit L-100 | 11.2 |
| Stearic Acid | 33.6 |
| Total | 120 |

TABLE 14

EX. 14

| Composition | Amt. (mg) per Capsule |
|---|---|
| Hydromorphone Hydrochloride | 8 |
| Eudragit RSPO | 36 |
| Eudragit L-100 | 6 |
| Stearic Acid | 18 |
| Talc | 52 |
| Total | 120 |

EXAMPLE 15

Figure 10:
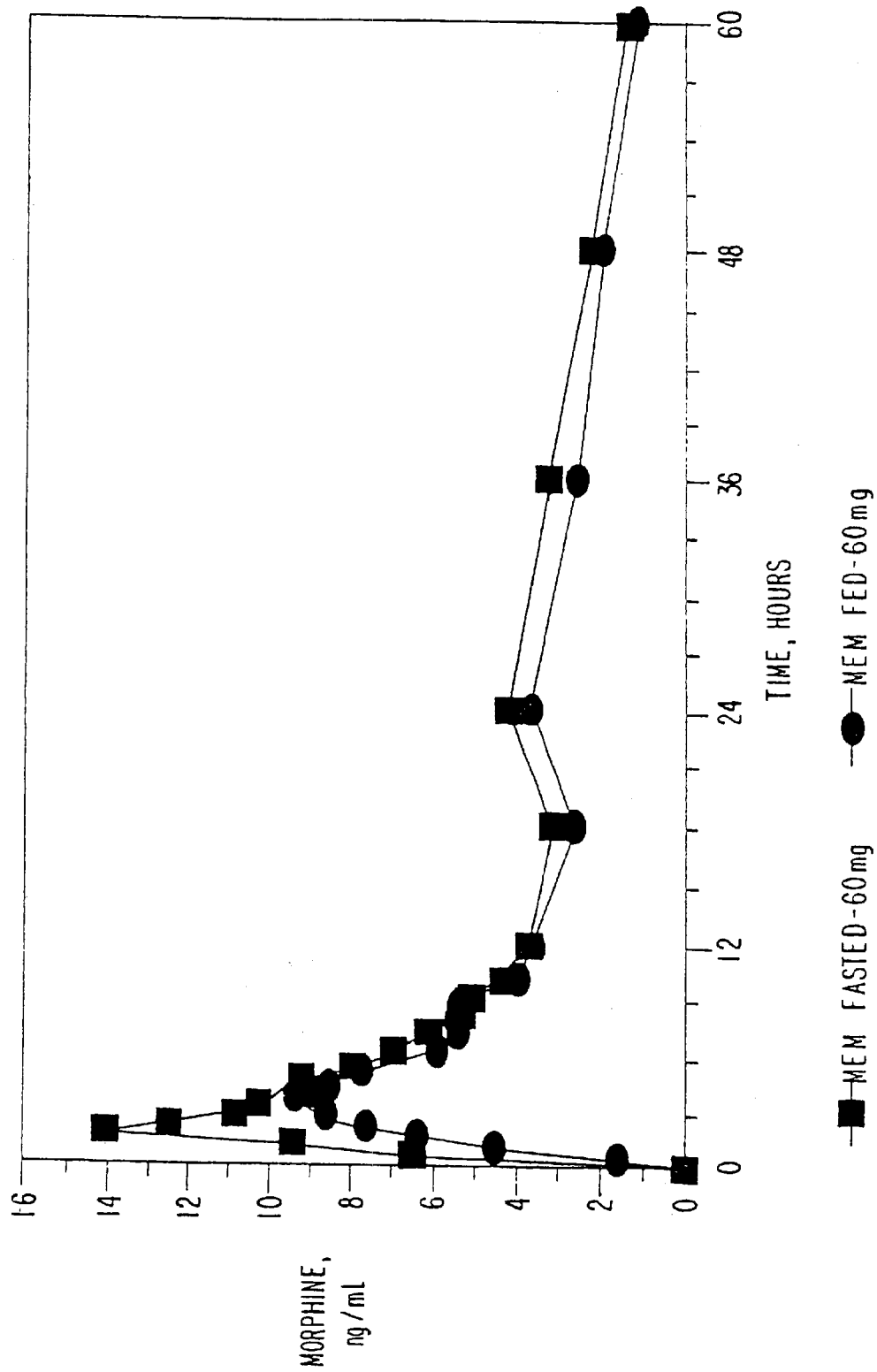
FIG. 10 is a graph displaying the results of Example 5.

In this Example, a bioavailability study was undertaken. Fourteen subjects were given the morphine sulphate formulations of Example 3. The results are provided in Table 15 below and in FIG. 10.

TABLE 15

| Group | AUC | $C_{max}$ | $T_{max}$ |
|---|---|---|---|
| Example 3 Fasted | 230 | 15.7 | 2.1 |
| Example 3 Fed | 213 | 14.0 | 3.2 |

From the above data, it can be seen that the formulation is an ideal candidate for an extended release or once-a-day product without a food effect.

The examples provided above are not meant to be exclusive. Many other variations of the present invention would be obvious to those skilled in the art, and are contemplated to be within the scope of the appended claims.

What is claimed is:

1. A unit dose sustained-release oral dosage form comprising a plurality of extruded particles, each of said particles comprising:
   an opioid analgesic dispersed in a matrix comprising
   one or more hydrophobic materials selected from the group consisting of acrylic polymers and alkylcelluloses;
   said particles being non-spheroidal and having a size from about 0.1 mm to about 12 mm and a diameter from about 0.1 mm to about 5 mm, said unit dose providing a release of said opioid analgesic over at least about 6 hours, said particles being formed by mixing the opioid analgesic and the one or more hydrophobic materials in an extruder to form said matrix, extruding the matrix in the extruder to form strands, and cutting said strands into said extruded particles.

2. A method of treating a patient with a sustained release multiparticulate formulation of a therapeutically active agent, comprising:
   (a) mixing together an opioid analgesic, and a hydrophobic material in an extruder to obtain a homogeneous mixture, the ratio of said hydrophobic material to said opioid analgesic in said mixture being sufficient to impart a release of said opioid analgesic from said particles over a time period of at least about 4 hours when said particle is exposed to an aqueous fluid;
   (b) heating said homogeneous mixture in the extruder;
   (c) extruding said homogeneous mixture with the extruder to thereby form strands;
   (d) cooling said strands containing said homogeneous mixture; and
   (e) cutting said strands into particles having a size from about 0.1 mm to about 12 mm; and
   (f) dividing said particles into unit doses; and administering said unit dose to a patient.

3. The unit dose of claim 1, wherein said opioid analgesic is selected from the group consisting of morphine, codeine, hydromorphone, hydrocodone, oxycodone, oxymorphone, dihydrocodeine, dihydromorphine, pharmaceutically acceptable salts thereof and mixtures thereof.

4. The unit dose of claim 1, wherein said opioid analgesic is selected from the group consisting of alfentanil, allylprodine, alphaprodine, anileridine, benzylmorphine, bezitramide, buprenorphine, butorphanol, clonitazene, codeine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levallorphan, levorphanol, levophenacyl morphan, lofentanil, meperidine, meptazinol, metazocine, methadone, metophon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tramadol, tilidine, pharmaceutically acceptable salts thereof and mixtures thereof.

5. The dosage form of claim 3, wherein said opioid analgesic consists of from about 2 mg to about 64 mg hydromorphone.

6. The dosage form of claim 3, wherein said opioid analgesic consists of from about 5 mg to about 800 mg morphine.

7. The dosage form of claim 3, wherein said opioid analgesic consists of from about 5 mg to about 400 mg oxycodone.

8. A method of preparing a multiparticulate sustained release oral dosage form, comprising:
(a) directly metering into an extruder a hydrophobic material and an opioid analgesic;
(b) heating said homogeneous mixture in the extruder;
(c) extruding said homogeneous mixture with the extruder to thereby form strands;
(d) cooling said strands containing said homogeneous mixture; and
(e) cutting said strands into particles having a size of from about 0.1 mm to about 12 mm; and
(f) dividing said particles into unit doses.

9. The unit dose of claim 1, wherein said acrylic polymer is comprised of monomers selected from the group consisting of an ester of acrylic acid, an ester of methacrylic acid, an alkyl ester of acrylic acid, an alkyl ester of methacrylic acid, and mixtures of any of the foregoing.

10. The unit dose of claim 1, further comprising a water insoluble binder.

11. The unit dose of claim 10, wherein said binder is selected from the group consisting of stearyl alcohol, stearic acid water insoluble waxes, fatty alcohols, hydrogenated fats, fatty acid esters. fatty acid glyercides, hydrocarbons, waxes, and hydrophobic and hydrophilic polymers having hydrocarbon backbones, and mixtures thereof.

12. An opioid unit dose sustained-release oral dosage form having substantially no feeding-fasting effect, comprising a plurality of extruded particles, each of said particles comprising:
an opioid analgesic dispersed in a matrix comprising:
one or more hydrophobic materials selected from the group consisting of acrylic polymers and alkylcelluloses;
said particles having a size from about 0.1 mm to about 12 mm and a diameter of from about 0.1 mm to about 3 mm, said unit dose providing a release of said opioid analgesic over at least about 12–24 hours, said particles being formed by mixing the opioid analgesic and the one or more hydrophobic materials in an extruder to form said matrix, extruding the matrix in the extruder to form strands, and cutting said strands into said extruded particles.

13. The unit dose of claim 1, wherein each of said particles comprise from about,1% to about 99% of said one or more hydrophobic materials.

14. The unit dose of claim 1, wherein each of said particles comprise from about 5% to about 95% of said one or more hydrophobic materials.

15. A method of preparing a multiparticulate sustained release oral dosage form, comprising:
(a) mixing together an opioid analgesic and one or more hydrophobic materials in an extruder to obtain a homogeneous mixture, the ratio of said one or more hydrophobic materials to said opioid analgesic in said mixture being sufficient to impart a release of said opioid analgesic from said particles over a time period of at least about 4 hours when said particle is exposed to an aqueous fluid;
(b) heating said homogeneous mixture in the extruder;
(c) extruding said homogeneous mixture with the extruder to thereby form strands;
(d) cooling said strands containing said homogeneous mixture; and
(e) cutting said strands into particles having a size from about 0.1 mm to about 12 mm; and
(f) dividing said particles into unit doses.

16. The method of claim 15, wherein said unit doses are placed into gelatin capsules.

17. The method of claim 15, wherein said homogenous mixture is heated to a temperature from about 30° C. to about 200° C. prior to extrusion.

18. The unit dose of claim 1, wherein the diameter of said particles is from about 0.1 mm to about 3 cm.

19. The method of claim 15, wherein said opioid analgesic is selected from the group consisting of morphine, codeine, hydromorphone, hydrocodone, oxycodone, oxymorphone, dihydrocodeine, dihydromorphine, pharmaceutically acceptable salts thereof and mixtures thereof.

20. The method of claim 15, wherein said opioid analgesic is selected from the group consisting of alfentanil, allylprodine, alphaprodine, anileridine, benzylmorphine, bezitramide, buprenorphine, butorphanol, clonitazene, codeine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levallorphan, levorphanol, levophenacyl morphan, lofentanil, meperidine, meptazinol, metazocine, methadone, metophon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tramadol, tilidine, pharmaceutically acceptable salts thereof and mixtures thereof.

21. The method of claim 15, wherein said opioid analgesic consists of from about 2 mg to about 64 mg hydromorphone or a pharmaceutically acceptable salt thereof.

22. The method of claim 15, wherein said opioid analgesic consists of from about 5 mg to about 800 mg morphine or a pharmaceutically acceptable salt thereof.

23. The method of claim 15, wherein said opioid analgesic consists of from about 5 mg to about 400 mg oxycodone or a pharmaceutically acceptable salt thereof.

24. A sustained release unit dose formulation comprising the particles prepared according to the method of claim 15.

25. The method of claim 15, wherein at least one of said one or more hydrophobic materials is an acrylic polymer comprised of monomers selected from the group consisting of an ester of acrylic acid, an ester of methacrylic acid, an alkyl ester of acrylic acid, an alkyl ester of methacrylic acid, and mixtures of any of the foregoing.

26. The method of claim 15, further comprising mixing a water insoluble binder with said opioid analgesic and said hydrophobic material in said extruder to obtain a homogeneous mixture.

27. The method of claim 26, wherein said binder is selected from the group consisting of stearyl alcohol, stearic acid water insoluble waxes fatty alcohols. hydrogenated fats, fatty acid esters, fatty acid glycerides, hydrocarbons, waxes, and hydrophobic and hydrophilic polymers having hydrocarbon backbones and mixtures thereof.

28. The method of claim 15, further comprising adjusting the aperture and aperture shape of the extruder to obtain a strand having a diameter from about 0.1 mm to about 3 cm.

29. An opioid unit dose sustained-release oral dosage form having substantially no feeding-fasting effect, comprising a plurality of extruded particles, each of said particles comprising:

an opioid analgesic dispersed in a matrix;

one or more hydrophobic materials selected from the group consisting of acrylic polymers. alkylcelluloses;

said particles having a size from about 0.1 mm to about 12 mm and a diameter of from about 0.1 mm to about 3 mm, said unit dose providing a release of said opioid analgesic over at least about 6 hours said particles being formed by mixing the opioid analgesic, and the one or more hydrophobic materials in an extruder to form said matrix, extruding the matrix in the extruder to form strands, and cutting said strands into said extruded particles.

30. The method of claim 2, further comprising mixing a water insoluble binder with said opioid analgesic and said hydrophobic material in said extruder to obtain a homogeneous mixture.

31. The method of claim 30, wherein said binder is selected from the group consisting of stearyl alcohol, stearic acid, water insoluble waxes, fatty alcohols, hydrogenated fats, fatty acid esters, fatty acid glycerides, hydrophobic and hydrophilic polymers having hydrocarbon backbones and mixtures thereof.

32. The method of claim 8, further comprising mixing a water insoluble binder with said opioid analgesic and said hydrophobic material in said extruder to obtain a homogeneous mixture.

33. The method of claim 32, wherein said binder is selected from the group consisting of stearyl alcohol, stearic acid, water insoluble waxes, fatty alcohols, hydrogenated fats, fatty acid esters, fatty acid glycerides, hydrophobic and hydrophilic polymers having hydrocarbon backbones and mixtures thereof.

34. The opioid unit dose of claim 12, further comprising a water insoluble binder.

35. The opioid unit dose of claim 34, wherein said binder is selected from the group consisting of stearyl alcohol, stearic acid, water insoluble waxes, fatty alcohols, hydrogenated fats, fatty acid esters, fatty acid glycerides, hydrophobic and hydrophilic polymers having hydrocarbon backbones and mixtures thereof.

36. The opioid unit dose of claim 29, further comprising a water insoluble binder.

37. The opioid unit dose of claim 36, wherein said binder is selected from the group consisting of stearyl alcohol, stearic acid, water insoluble waxes, fatty alcohols, hydrogenated fats, fatty acid esters, fatty acid glycerides, hydrophobic and hydrophilic polymers having hydrocarbon backbones and mixtures thereof.

38. The unit dose of claim 4 wherein said opioid analgesic is tramadol or a pharmaceutically acceptable salt thereof.

39. The method of claim 20 wherein said opioid analgesic is tramadol or a pharmaceutically acceptable salt thereof.

40. The method of claim 2 wherein said opioid analgesic is tramadol or a pharmaceutically acceptable salt thereof.

41. The method of claim 8 wherein said opioid analgesic is tramadol or a pharmaceutically acceptable salt thereof.

42. The unit dose of claim 12 wherein said opioid analgesic is tramadol or a pharmaceutically acceptable salt thereof.

43. The unit dose of claim 29 wherein said opioid analgesic is tramadol or a pharmaceutically acceptable salt thereof.

* * * * *

UNITED STATES PATENT AND TRADEMARK OFFICE
CERTIFICATE OF CORRECTION

PATENT NO. : 6,335,033 B2
DATED : January 1, 2002
INVENTOR(S) : Benjamin Oshlack et al.

It is certified that error appears in the above-identified patent and that said Letters Patent is hereby corrected as shown below:

Drawings,
Figures 1-10, should be replaced with Figures 1-9, enclosed herewith, as originally filed with the parent application U.S. Application Serial No. 08/334,209, now U.S. Patent No. 5,965,161, to which the instant Patent claims priority.

Column 2,
Line 61, "FIGS. 3 and 4" should read -- FIGS. 3a and 3b --;
Line 62, "Examples 3,4 and 6" should read -- Examples 3 and 5 --;
Line 65, "Examples 7 and 8" should read -- Examples 5,7 and 8 --;
Line 67, "Examples 6,7 and 8" should read -- Examples 9 and 10--.

Column 3,
Line 2, "Examples 9 and 10" should read -- Examples 11 and 12 --;
Line 5, "Examples 11 and 12" should read -- Examples 13 and 14 --;
Lines 6 and 7, "graph displaying the dissolution results of Examples 15 and 16" should read -- schematic representation of a system for carrying out the present invention; and --;
Lines 8 and 9, "schematic representation of a system for carrying out the present invention; and" should read -- graph displaying the results of Example 15. --.
Line 10, beginning with "FIG.10" should be deleted.

Column 8,
Line 66, "FIG. 9" should read -- FIG. 8 --.

Column 11,
Line 26, "FIG. 3" should read -- FIG. 3a --;
Line 31, "FIG. 4" should read -- FIG. 3b --.

UNITED STATES PATENT AND TRADEMARK OFFICE
CERTIFICATE OF CORRECTION

PATENT NO. : 6,335,033 B2
DATED : January 1, 2002
INVENTOR(S) : Benjamin Oshlack et al.

It is certified that error appears in the above-identified patent and that said Letters Patent is hereby corrected as shown below:

Column 12,
Line 16, "FIG. 6" should read -- FIG. 5 --;
Line 54, "FIG. 7" should read -- FIG. 6 --.

Column 13,
Line 21, "FIG. 8" should read -- FIG. 7 --;
Line 52, "FIG. 10" should read -- FIG. 9 --.

Signed and Sealed this

Seventeenth Day of August, 2004

JON W. DUDAS
*Acting Director of the United States Patent and Trademark Office*